(12) United States Patent
Lee et al.

(10) Patent No.: US 9,279,759 B2
(45) Date of Patent: Mar. 8, 2016

(54) NANOPARTICLE ARRAY WITH TUNABLE NANOPARTICLE SIZE AND SEPARATION

(71) Applicants: Woonjoo Lee, Daejeon (KR); Seung Yong Lee, North Bethesda, MD (US); Oded Rabin, Washington, DC (US); Robert M. Briber, Bethesda, MD (US); Xin Zhang, College Park, MD (US)

(72) Inventors: Woonjoo Lee, Daejeon (KR); Seung Yong Lee, North Bethesda, MD (US); Oded Rabin, Washington, DC (US); Robert M. Briber, Bethesda, MD (US); Xin Zhang, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 63 days.

(21) Appl. No.: 13/986,424

(22) Filed: May 1, 2013

(65) Prior Publication Data

US 2013/0293884 A1    Nov. 7, 2013

Related U.S. Application Data

(60) Provisional application No. 61/803,017, filed on Mar. 18, 2013, provisional application No. 61/774,341, filed on Mar. 7, 2013, provisional application No. 61/641,155, filed on May 1, 2012.

(51) Int. Cl.
| | |
|---|---|
| *G01N 21/01* | (2006.01) |
| *G01N 21/65* | (2006.01) |
| *B05D 3/10* | (2006.01) |
| *G01N 21/64* | (2006.01) |

(52) U.S. Cl.
CPC ........... *G01N 21/01* (2013.01); *B05D 3/10* (2013.01); *B05D 3/101* (2013.01); *G01N 21/658* (2013.01); *G01N 21/648* (2013.01); *Y10T 428/24893* (2015.01)

(58) Field of Classification Search
None
See application file for complete search history.

(56) References Cited

U.S. PATENT DOCUMENTS

2005/0196870 A1* 9/2005 Sun .............................. 436/166

OTHER PUBLICATIONS

Zhao et al, Nature Materials 8 pp. 979-985, published online Oct. 18, 2009.*
Ishizu, Polymer Preprints, 40(1), pp. 456-457, 1999.*
Abramoff, M.D., et al., "Image Processing with ImageJ," *Biophotonics International* 11(7):36-42, Laurin Publishing Co. Inc., United States (2004).
Aizawa, M., et al., "Block Copolymer Templated Chemistry for the Formation of Metallic Nanoparticle Arrays on Semiconductor Surfaces," *Chem. Mater* 19:5090-5101, American Chemical Society, United States (2007).

(Continued)

*Primary Examiner* — Erma Cameron
(74) *Attorney, Agent, or Firm* — Sterne, Kessler, Goldstein & Fox PLLC

(57) ABSTRACT

The present invention is directed to self-assembled nanoparticle arrays, methods of making the nanoparticle arrays, and methods of using the nanoparticle arrays in spectroscopic methods for detecting targets of interest. The present invention is also directed to a fabrication method for surface-enhanced Raman scattering (SERS) substrates that possess a unique combination of three highly desirable attributes: (a) the SERS substrates can be tuned to match the laser wavelength of operation and maximize the enhancement factor for the particular Raman instrument and analyte in use; (b) the SERS substrates have a highly reproducible enhancement factor over macroscopic sampling areas; and (c) the fabrication method is achieved without resorting to expensive, slow nano-lithography tools.

12 Claims, 23 Drawing Sheets
(1 of 23 Drawing Sheet(s) Filed in Color)

(56) References Cited

OTHER PUBLICATIONS

Alexander, K.D., et al., "A high-throughput method for controlled hot-spot fabrication in SERS-active gold nanoparticle dimer arrays," *J. Raman Spectrosc. 40*:2171-2175, John Wiley & Sons, Ltd., United States (2009).

Antonietti, M., et al., "Determination of the Micelle Architecture of Polystyrene/Poly(4-vinylpyridine) Block Copolymers in Dilute Solution," *Macromolecules 27*:3276-3281, American Chemical Society, United States (1994).

Banerjee, P., et al., "Plasmon-Induced Electrical Conduction in Molecular Devices," *ACS Nano 4*(2):1019-1025, American Chemical Society, United States (2010).

Bates, F.S. and Fredrickson, G.H., "Block Copolymer Thermodynamics: Theory and Experiment," *Annu. Rev. Phys. Chem. 41*:525-557, Annual Reviews Inc., United States (1990).

Baumberg, J.J., et al., "Angle-Resolved Surface-Enhanced Raman Scattering on Metallic Nanostructured Plasmonic Crystals," *Nano Letters 5*(11):2262-2267, American Chemical Society, United States (2005).

Böltau, M., et al., "Surface-induced structure formation of polymer blends on patterned substrates," *Nature 391*:877-879, Nature Publishing Group, United Kingdom (1998).

Brown, R.J.C. and Milton, M.J.T., "Nanostructures and nanostructured substrates for surface-enhanced Raman scattering (SERS)," *J. Raman Spectrosc. 39*:1313-1326, John Wiley & Sons, Ltd., United States (2008).

Camden, J.P., et al., "Controlled Plasmonic Nanostructures for Surface-Enhanced Spectroscopy and Sensing," *Accounts of Chemical Research 41*(12):1653-1661, American Chemical Society, United States (2008).

Chan, C.K., et al., "High-performance lithium battery anodes using silicon nanowires," *Nature Nanotechnology 3*:31-35, Nature Publishing Group, United Kingdom (2008).

Chiu, J.J., et al., "Control of Nanoparticle Location in Block Copolymers," *J. Am. Chem. Soc. 127*:5036-5037, American Chemical Society, United States (2005).

Chu, Y., et al., "Double-Resonance Plasmon Substrates for Surface-Enhanced Raman Scattering with Enhancement at Excitation and Stokes Frequencies," *ACS Nano 4*(5):2804-2810, American Chemical Society, United States (2010).

Cui, L., et al., "Ordered porous polymer films via phase separation in humidity environment," *Polymer 46*:5334-5340, Elsevier Ltd., Netherlands (2005).

Darling, S.B., et al., "Self-Organization of FePt Nanoparticles on Photochemically Modified Diblock Copolymer Templates," *Adv. Mater. 17*:2446-2450, Wiley-VCH, Germany (2005).

Darling, S.B., "Mechanism for hierarchical self-assembly of nanoparticles on scaffolds derived from block copolymers," *Surface Science 601*:2555-2561, Elsevier B.V., Netherlands (2006).

Darling, S.B., "Directing the self-assembly of block copolymers," *Prog. Polym. Sci. 32*:1152-1204, Elsevier Ltd., Netherlands (2007).

Dick, L.A., et al., "Metal Film over Nanosphere (MFON) Electrodes for Surface-Enhanced Raman Spectroscopy (SERS): Improvements in Surface Nanostructure Stability and Suppression of Irreversible Loss," *J. Phys. Chem. B 106*:853-860, American Chemical Society, United States (2002).

Eychmüller, A., "Structure and Photophysics of Semiconductor Nanocrystals," *J. Phys. Chem. B 104*:6514-6528, American Chemical Society, United States (2000).

Farcau, C. and Astilean, S., "Mapping the SERS Efficiency and Hot-Spots Localization on Gold Film over Nanospheres Substrates," *J. Phys. Chem. C 114*:11717-11722, American Chemical Society, United States (2010).

Félidj, N., et al., "Optimized surface-enhanced Raman scattering on gold nanoparticle arrays," *Appl. Phys Lett. 82*(18):3095-3097, American Institute of Physics, United States (2003).

Freeman, R.G., et al., "Self-Assembled Metal Colloid Monolayers: An Approach to SERS Substrates," *Science 267*(5204):1629-1632, American Association for the Advancement of Science, United States (1995).

Fromm, D.P., et al., "Exploring the chemical enhancement for surface-enhanced Raman scattering with Au bowtie nanoantennas," *J. Chem. Phys. 124*:061101, American Institute of Physics, United States (2006).

Genov, D.A., et al., "Resonant Field Enhancements from Metal Nanoparticle Arrays," *Nano Lett. 4*(1):153-158, American Chemical Society, United States (2004).

Gersten, J. and Nitzan, A., "Electromagnetic theory of enhanced Raman scattering by molecules absorbed on rough surfaces," *J. Chem. Phys. 73*(7):3023-3037, American Institute of Physics, United States (1980).

Glass, R., et al., "Micro-Nanostructured Interfaces Fabricated by the Use of Inorganic Block Copolymer Micellar Monolayers as Negative Resist for Electron-Beam Lithography," *Adv. Funct. Mater. 13*(7):569-575, Wiley-VCH, Germany (2003).

Hatab, N.A., et al., "Free-Standing Optical Gold Bowtie Nanoantenna with Variable Gap Size for Enhanced Raman Spectroscopy," *Nano Lett. 10*:4952-4955, American Chemical Society, United States (2010).

Haynes, C.L., et al., "Nanoparticle Optics: The Importance of Radiative Dipole Coupling in Two-Dimensional Nanoparticle Arrays," *J. Phys. Chem B 107*:7337-7342, American Chemical Society, United States (2003).

Hu, F.X., et al., "Antibacterial and Antifungal Efficacy of Surface Functionalized Polymeric Beads in Repeated Applications," *Biotechnology and Bioengineering 89*(4):474-484, Wiley Periodicals, Inc., United States (2004).

Huang, J., et al., "A General Method for Assembling Single Colloidal Particle Lines," *Nano Lett. 6*(3):524-529, American Chemical Society, United States (2006).

Hwang, W., et al., "Micropatterning of block copolymer micelle thin films using solvent capillary contact printing," *Nanotechnology 16*:2897-2902, IOP Publishing Ltd., United Kingdom (2005).

Jain, P.K., et al., "On the Universal Scaling Behavior of the Distance Decay of Plasmon Coupling in Metal Nanoparticle Pairs: A Plasmon Ruler Equation," *Nano Lett. 7*(7):2080-2088, American Chemical Society, United States (2007).

Jensen, T.R., et al., "Nanosphere Lithography: Tunable Localized Surface Plasmon Resonance Spectra of Silver Nanoparticles," *J. Phys. Chem B 104*:10549-10556, American Chemical Society, United States (2000).

Kim, D.H., et al., "Inorganic Nanodots from Thin Films of Block Copolymers," *Nano Lett. 4*(I0):1841-1844, American Chemical Society, United States (2004).

Kim, S.H., et al., "Highly Oriented and Ordered Arrays from Block Copolymers via Solvent Evaporation," *Adv. Mater. 16*(3):226-231, Wiley-VCH, Germany (2004).

Ko, H., et al., "Nanostructured Surfaces and Assemblies as SERS Media," *Small 4*(10):1576-1599, Wiley-VCH, Germany (2008).

Krishnamoorthy, S., et al., "Tuning the Dimensions and Periodicities of Nanostructures Starting from the Same Polystyrene-block-poly(2-vinylpyridine) Diblock Copolymer," *Adv. Funct. Mater. 16*:1469-1475, Wiley-VCH, Germany (2006).

Lam, Y.M., et al., "Controlled chemical stabilization of self-assembled PS-P4VP nanostructures," *J. Colloid and Interface Science 317*:255-263, Elsevier Inc., Netherlands (2007).

Lee, D.H., et al., "Hierarchically Organized Carbon Nanotube Arrays from Self-Assembled Block Copolymer Nanotemplates,", *Adv. Mater. 20*:2480-2485, Wiley-VCH, Germany (2008).

Lee, S.Y., et al., "Dispersion in the SERS Enhancement with Silver Nanocube Dimers," *ACS Nano 4*(10):5763-5772, American Chemical Society, United States (2010).

Lin, Y., et al., "Self-directed self-assembly of nanoparticle/copolymer mixtures," *Nature 434*:55-59, Nature Publishing Group, United Kingdom (2005).

Lohmueller, T., et al., "Synthesis of Quasi-Hexagonal Ordered Arrays of Metallic Nanoparticles with Tuneable Particle Size," *Adv. Mater. 20*:2297-2302, Wiley-VCH, Germany (2008).

(56) References Cited

OTHER PUBLICATIONS

Lu, J., et al., "Fabrication of Ordered Catalytically Active Nanoparticles Derived from Block Copolymer Micelle Templates for Controllable Synthesis of Single-Walled Carbon Nanotubes," *J. Phys. Chem B 110*:6655-6660, American Chemical Society, United States (2006).

Mayergoyz, I.D., et al., "Analysis of Dynamics of Excitation and Dephasing of Plasmon Resonance Modes in Nanoparticles," *Physical Review Letters 98*:147401, The American Physical Society, United States (2007).

McFarland, A.D., et al., "Wavelength-Scanned Surface-Enhanced Raman Excitation Spectroscopy," *J. Phys. Chem. B 109*:11279-11285, American Chemical Society, United States (2005).

McMahon, J.M., et al., "Gold nanoparticle dimer plasmonics: finite element method calculations of the electromagnetic enhancement to surface-enhanced Raman spectroscopy," *Anal Bioanal Chem 394*:1819-1825, Springer-Verlag, Germany (2009).

Mu, C., et al., "Au nanoparticle arrays with tunable particle gaps by template-assisted electroless deposition for high performance surface-enhanced Raman scattering," *Nanotechnology 21*:015604, IOP Publishing Ltd., United Kingdom (2010).

Nie, Z., et al., "Properties and emerging applications of self-assembled structures made from inorganic nanoparticles," *Nature Nanotechnology 5*:15-25, Macmillan Publishers Limited, United Kingdom (2010).

Park, S., et al., "Solvent-Induced Transition from Micelles in Solution to Cylindrical Microdomains in Diblock Copolymer Thin Films," *Macromolecules 40*:9059-9063, American Chemical Society, United States (2007).

Peinemann, K-V., et al., "Asymmetric superstructure formed in a block copolymer via phase separation," *Nature Materials 6*:992-996, Nature Publishing Group, United Kingdom (2007).

Rao, C.N.R., and Cheetham, A.K., "Science and technology of nanomaterials: current status and future prospects," *J. Mater. Chem. 11*:2887-2894, The Royal Society of Chemistry, United Kingdom (2001).

Sau, T.K. and Murphy, C.J., "Seeded High Yield Synthesis of Short Au Nanorods in Aqueous Solution," *Langmuir 20*:6414-6420, American Chemical Society, United States (2004).

Schatz, G.C., et al., "Electromagnetic Mechanism of SERS," *Topics Appl. Phys. 103*:19-46, Springer-Verlag, Germany (2006).

Shenhar, R. and Rotello, V.M., "Nanoparticles: Scaffolds and Building Blocks," *Acc. Chem. Res. 36*:549-561, American Chemical Society, United States (2003).

Sohn, B.H. and Seo, B.H., "Fabrication of the Multilayered Nanostructure of Alternating Polymers and Gold Nanoparticles with Thin Films of Self-Assembling Diblock Copolymers," *Chem. Mater. 13*:1752-1757, American Chemical Society, United States (2001).

Stoerzinger, K.A., et al., "Screening Nanopyramid Assemblies to Optimize Surface Enhanced Raman Scattering," *J. Phys. Chem. Lett. 1*:1046-1050, American Chemical Society, United States (2010).

Tanaka, K., et al., "Film Thickness Dependence of the Surface Structure of Immiscible Polystyrene/Poly(methyl methacrylate) Blends," *Macromolecules 29*:3232-3239, American Chemical Society, United States (1996).

Walheim, S., et al., "Structure Formation via Polymer Demixing in Spin-Cast Films," *Macromolecules 30*:4995-5003, American Chemical Society, United States (1997).

Walheim, S., et al., "Nanophase-Separated Polymer Films as High-Performance Antireflection Coatings," *Science 283*:520-522, American Association for the Advancement of Science, United States (1999).

Wang, Y. and Voth, G.A., "Unique Spatial Heterogeneity in Ionic Liquids," *J. Am. Chem. Soc. 127*:12192-12193, American Chemical Society, United States (2005).

Wang, H-H., et al., "Highly Raman-Enhancing Substrates Based on Silver Nanoparticle Arrays with Tunable Sub-10 nm Gaps," *Adv. Mater. 18*:491-495, Wiley-VCH, Germany (2006).

Wang, H., et al., "Plasmonic Nanoshell Arrays Combine Surface-Enhanced Vibrational Spectroscopies on a Single Substrate," *Angew. Chem. Int. Ed. 46*:9040-9044, Wiley-VCH, Germany (2007).

Ward, D.R., et al., "Electromigrated Nanoscale Gaps for Surface-Enhanced Raman Spectroscopy," *Nano Lett. 7*(5): 1396-1400, American Chemical Society, United States (2007).

Wei, A., et al., "Tunable Surface-Enhanced Raman Scattering from Large Gold Nanoparticle Arrays," *ChemPhysChem 12*:743-745, Wiley-VCH, Germany (2001).

Yan, B., et al., "Engineered SERS Substrates with Multiscale Signal Enhancement: Nanoparticle Cluster Arrays," *ACS Nano 3*(5):1190-1202, American Chemical Society, United States (2009).

Yan, C., et al., "Mechanical and Environmental Stability of Polymer Thin-Film-Coated Graphene," *ACS Nano 6*(3):2096-2103, American Chemical Society, United States (2011).

Yun, S-H., et al., "Tunable Magnetic Arrangement of Iron Oxide Nanoparticles in Situ Synthesized on the Solid Substrate from Diblock Copolymer Micelles," *Langmuir 21*:6548-6552, American Chemical Society, United States (2005).

Zhao, J., et al., "Wavelength-Scanned Surface-Enhanced Resonance Raman Excitation Spectroscopy," *J. Phys. Chem. C 112*:19302-19310, American Chemical Society, United States (2008).

* cited by examiner

NANOPARTICLE ARRAY WITH TUNABLE NANOPARTICLE SIZE AND SEPARATION

CROSS-REFERENCE TO RELATED APPLICATIONS

This application claims the benefit of U.S. Provisional Application No. 61/641,155, filed May 1, 2012, U.S. Provisional Application No. 61/774,341, filed Mar. 7, 2013, and U.S. Provisional Application No. 61/803,017, filed Mar. 18, 2013.

STATEMENT REGARDING FEDERALLY SPONSORED RESEARCH OR DEVELOPMENT

This invention was made with government support under 70NANB5H1153 awarded by the National Institute of Standards and Technology and under N000140911190 awarded by the Office of Naval Research. The government has certain rights to this invention.

BACKGROUND OF THE INVENTION

1. Field of the Invention

The present invention is directed to self-assembled nanoparticle arrays, methods of making the nanoparticle arrays, and methods of using the nanoparticle arrays in spectroscopic methods for detecting targets of interest.

2. Background

Plasmonic structures are routinely used in Raman spectroscopy to increase the cross-section for the scattering process and augment the signal, particularly when very little sample is available, a technique termed surface-enhanced Raman scattering (SERS) (Brown, R. J. C., et al., *J. Raman Spectrosc.* 39:1313 (2008); Camden, J. P., et al., *Acc. Chem. Res.* 41:1653 (2008)). The extreme sensitivity of SERS is achieved through the strong coupling between electromagnetic radiation, plasmon modes of a surface, and electronic states of a molecule, which in turn couple to the vibrational modes of the molecule (J. Gersten and A. Nitzan, *J. Chem. Phys.* 73:3023 (1980); Schatz, G., et al., in Surface-Enhanced Raman Scattering—Physics and Applications, *Topics Appl. Phys.* 103:19 (2006)). The SERS substrate, containing the plasmonic structure and often a binding site for the molecule to be analyzed, needs to be tailored precisely (i.e., at the nanoscale) in order to achieve efficient coupling and provide colossal signal enhancement (Ko, H., et al., *Small* 4:1576 (2008)). In many cases, it is desirable to design the SERS substrate so that its surface plasmon resonance frequency lies between the frequencies of the incident light (the laser of the Raman spectrometer) and the scattered light (McFarland, A. D., et al., *J. Phys. Chem. B* 109:11279 (2005); Chu, Y. Z., et al., *ACS Nano* 4:2804 (2010); Felidj, N., et al., *Appl. Phys. Lett.* 82:3095 (2003)). The surface plasmon resonance frequency may also need to match approximately an electronic transition energy of the molecule or solid being probed to make use of the resonant Raman scattering effect and further increase the enhancement factor (Zhao, J., et al., *J. Phys. Chem. C* 112:19302 (2008)). Self-assembly techniques (Freeman, R. G., et al., *Science* 267:1629 (1995); Wang, H., et al., *J. Am. Chem. Soc.* 127:14992 (2005); Wang, H., et al., *Angew. Chem. Int. Ed* 46:9040 (2007); Wei, A., et al., *Chem Phys Chem* 2:743 (2001); Mu, C., et al., *Nanotechnology* 21:015604 (2010); Dick, L. A., et al., *J. Phys. Chem. B* 106:853 (2001); Baumberg, J. J., et al., *Nano Lett.* 5:2262 (2005)), nano-lithography techniques (Felidj, N., et al., *Appl. Phys. Lett.* 82:3095 (2003); Hatab, N. A., et al., *Nano Lett.* 7:4952 (2010); Fromm, D. P., et al., *J. Chem. Phys.* 124:061101 (2006); Ward, D. R., et al., *Nano Lett.* 7:1396 (2007)), and combinations thereof (Alexander, K. D., et al., *J. Raman Spectrosc.* 40:2171 (2009); Yan, B., et al., *ACS Nano* 3:1190 (2009); Stoerzinger, K. A., et al., *J. Phys. Chem. Lett.* 1:1046 (2010); Lee, S. Y., et al., *ACS Nano* 4:5763 (2010)) have been employed to fabricate and optimize SERS substrates for the detection of and discrimination between analytes. Each fabrication method for SERS substrates involves a compromise between enhancement factor, cost, active area, reproducibility, and service life.

Nanoparticles show unique optical, magnetic, and electric properties, which are often size or shape dependent and different from the properties of the respective bulk material (R. Shenhar and V. M. Rotello, *Acc. Chem. Res.* 36:549 (2003); Shipway, A. N., et al., *Chem Phys Chem.* 1:18 (2000); Nie, Z. H., et al., *Nature Nanotechnol.* 5:15 (2010); Eychmuller, A., *J. Phys. Chem. B* 104:6514 (2000); C. N. R. Rao and A. K. Cheetham, *J. Mater. Chem.* 11:2887 (2001)). As these properties often only emerge when appropriate phenomena of coupling and exchange between the nanoparticles exist, the nanoparticle position distribution generally needs to be controlled through immobilization and assembly of the nanoparticles on a substrate or in a medium. Recently, various polymer/nanoparticle hierarchical structures have been introduced as candidates for use in next generation applications in electronic devices and sensors (Chiu, J. J., et al., *J. Am. Chem. Soc.* 127:5036 (2005); B. H. Sohn and B. H. Seo, *Chem. Mater.* 13:1752 (2001); Lin, Y., et al., *Nature* 434:55 (2005)). The use of block copolymers to produce nanoscale templates has gained increasing attention as the block copolymer morphology is determined by the volume fraction of the polymer blocks, and the size and the distance between domains is determined by the overall molecular weight (F. S. Bates and G. H. Fredrickson, *Annu. Rev. Phys. Chem.* 41:525 (1990)). Thus, block copolymers can be utilized as templates for controlling the spatial location of nanoparticles (S. B. Darling, *Prog. Polym. Sci.* 32:1152 (2007); Darling, S. B., et al., *Adv. Mater.* 17:2446 (2005); S. B. Darling, *Surf Sci.* 601:2555 (2007)). Among the processing techniques available for directing the self-assembly of block copolymer thin films, controlling the rate of solvent evaporation has attracted particular attention as it is simple and generally not sensitive to the substrate. An example is provided by polystyrene-b-poly (ethylene oxide) (PS-b-PEO) diblock copolymer having cylindrical microdomains of PEO. After solvent annealing, defect-free lateral ordering of vertically oriented PEO cylinders can be achieved over several micrometers (Kim, S. H., et al., *Adv. Mater.* 16:226 (2004)). Kim et al. have reported a simple route for fabricating a nanopatterned array of inorganic oxide semiconductors using the PS-b-PEO film as a template (Kim, D. H., et al., *Nano Lett.* 4:1841 (2004)). In the film, the PEO forms hexagonally ordered domains with a 2 nm depression in each of the PEO domains, where semiconductors such as silica and titania were grown by exposure to precursor vapor. Polystyrene-b-poly(4-vinylpyridine) (PS-b-P4VP) has been used to synthesize nanoparticles by exploiting specific interactions between the P4VP block and metallic precursors (M. Aizawa and J. M. Buriak, *Chem. Mater.* 19:5090 (2007); Glass, R., et al., *Adv. Funct. Mater.* 13:569 (2003); Lohmueller, T., et al., *Adv. Mater.* 20:2297 (2008); Yun, S. H., et al., *Langmuir* 21:6548 (2005)). Typically, metallic precursor loaded PS-b-P4VP micelles are deposited onto a substrate by spin-coating or dip coating. Subsequent plasma treatment converts the precursors to nanoparticles and eliminates the polymer; the result is a hexagonal array of nanoparticles that matches the micellar monolayer present before plasma treatment. Metal nanoparticles have been widely used as catalysts for the growth of nanowires and nanotubes (Chan, C. K., et al., *Nature Nanotechnol.* 3:31 (2008); Huang, J. X., et al., *Nano Lett.* 6:524 (2006); Lee., D. H., et al., *Adv. Mater.* 20:2480 (2008); Lu., J., et al., *J. Phys. Chem. B* 110:6655 (2006)), in sensors using surface enhanced Raman scattering (Freeman, R. G., et al., *Science* 267:1629 (1995); Yan, B., et al., *ACS Nano* 3:1190 (2009)), and for optoelectronics (Banerjee, P., et al., *ACS Nano* 4:1019 (2010)). However, as there was no covalent or electrostatic interaction between the plasma generated metal nanoparticles and the substrate, nanoparticle detachment from the substrate leads to the loss of the pattern (Lohmueller, T., et al., *Adv. Mater.* 20:2297 (2008)).

The present invention provides a fabrication method for nanoparticle arrays with tunable nanoparticles size and tunable separation between adjacent nanoparticles. The method applies to all nanoparticles that can be immobilized on at least one of the polymer blocks. Therefore, nanoparticles with useful electrical, optical, magnetic, chemical and catalytic properties can be used to form the arrays.

The present invention provides a fabrication method for SERS substrates that possess a unique combination of three highly desirable attributes: (a) the SERS substrates can be tuned to match the laser wavelength of operation and maximize the enhancement factor for the particular Raman instrument and analyte in use; (b) the SERS substrates have a highly reproducible enhancement factor over macroscopic sampling areas; and (c) the fabrication method is achieved without resorting to expensive, slow nano-lithography tools. The substrates are made entirely through self-assembly and templating techniques, which are cost-effective and scalable to large areas. These attributes make the fabrication process very appealing for mass production. Similarly, the present invention provides a fabrication method for substrates for other surface enhanced spectroscopic techniques, such as surface enhanced fluorescence, surface enhance (infrared) absorption, surface enhance (Raman) optical activity, and surface enhanced circular dichroism.

The present invention provides a fabrication method for magnetic media substrates for information storage. The magnetic nanoparticles arrays can be produced with densities of at least $2\times10^{11}$ nanoparticles/cm$^2$ uniformly over large areas. The substrates are made entirely through self-assembly and templating techniques, which are cost-effective and scalable to large areas.

BRIEF SUMMARY OF THE INVENTION

In some embodiments, the present invention provides a nanoparticle array comprising:
  (a) a block copolymer applied to a substrate, wherein the block copolymer comprises at least two polymer blocks, and wherein at least one of the polymer blocks has been functionalized; and
  (b) a plurality of nanoparticles on the block copolymer, wherein the nanoparticles are dispersed on the block copolymer, and wherein the nanoparticles adhere to at least 90% of the block copolymer domains that have been functionalized.

In some embodiments, the block copolymer comprises a first polymer block and a second polymer block.

In some embodiments, the first polymer block is polystyrene.

In some embodiments, the second polymer block is poly(4-vinylpyridine) or poly(2-vinylpyridine).

In some embodiments, the first polymer block is polystyrene and the second polymer block is poly(4-vinylpyridine).

In some embodiments, the nanoparticle array is regular and substantially free of defects.

In some embodiments, the nanoparticle array is used for surface-enhanced Raman scattering, surface-enhanced infrared absorption, surface-enhanced fluorescence, surface-enhanced Raman optical activity, or surface-enhanced circular dichroism.

In some embodiments, the present invention provides a method of producing a nanoparticle array comprising:
  (a) applying a block copolymer onto a substrate to give a thin film;
  (b) reacting the applied block copolymer with a functionalizing agent; and
  (c) immersing the thin film of (b) in a nanoparticle suspension to give a nanoparticle array;
wherein the nanoparticles are dispersed on the block copolymer.

In some embodiments, the present invention provides a method of producing a nanoparticle array comprising:
  (a) applying a block copolymer onto a substrate to give a thin film;
  (b) reacting the applied block copolymer with a functionalizing agent;
  (c) immersing the thin film in a nanoparticle suspension to provide a nanoparticle array disposed on the thin film; and
  (d) immersing the nanoparticle array in a growth solution;
wherein the nanoparticles are dispersed on the block copolymer.

In some embodiments, application of a block copolymer onto a substrate is followed by solvent vapor annealing or thermal annealing.

In some embodiments, the substrate is selected from the group consisting of a metal, an alloy, a ceramic, a semiconductor, a plastic, a composite, a natural fiber, a synthetic fiber, glass, silicon, paper, wood, fabric, and quartz.

In some embodiments, the functionalizing agent is selected from the group consisting of benzyl bromide, benzyl chloride, 1,4-dibromobutane, 1,5-dibromopentane, 1,6-dibromohexane, 1,7-dibromoheptane, 1,8-dibromooctane, 1,9-dibromononane, 1,4-dichlorobutane, 1,5-dichloropentane, 1,6-dichlorohexane, 1,7-dichloroheptane, 1,8-dichlorooctane, 1,9-dichlorononane, and combinations thereof.

In some embodiments, the nanoparticle suspension comprises nanoparticles selected from the group consisting of Au, Ag, Pt, Cu, $Cu_2S$, CdS, CdSe, CdTe, ZnS, ZnSe, ZnTe, GaN, GaP, GaAs, GaSb, AlN, AlP, AlAs, AlSb, InP, InAs, InSb, $Fe_3O_4$, $Co_3O_4$, $NiFe_2O_4$, $CoFe_2O_4$, FePt, CoPt, FeNi, FeCo, Co, CoO, Ni, and NiO nanoparticles.

In some embodiments, the growth solution comprises a metal atom selected from the group consisting of Ag, Au, Cu, and Li or a non-metal selected from the group consisting of $SiO_2$, $TiO_2$, $Fe_2O_3$, $Al_2O_3$, Cds, CdSe, PbS, PbSe, and $Bi_2S_3$.

In some embodiments, the present invention provides a method for enhancing a Raman signal of an analyte comprising:
  (a) providing a nanoparticle array comprising:
    (1) a block copolymer applied to a substrate, wherein the block copolymer comprises at least two polymer blocks, and wherein at least one of the polymer blocks has been functionalized; and
    (2) a plurality of nanoparticles on the block copolymer, wherein the nanoparticles are dispersed on the block copolymer, and wherein the nanoparticles adhere to at least 90% of the block copolymer domains that have been functionalized;
(b) adhering an analyte to the nanoparticle array;
(c) exposing the analyte to incident light of an excitation wavelength that overlaps with the metallic nanoparticle plasmon resonance band; and
(d) detecting the optical signal of the analyte as Raman scattered radiation;

wherein the optical signal of the analyte is enhanced compared to the signal when the analyte is exposed to incident light in the absence of the nanoparticle array.

In some embodiments, the present invention provides a method of detecting an analyte comprising:
(a) providing a nanoparticle array comprising:
  (1) a block copolymer applied to a substrate, wherein the block copolymer comprises at least two polymer blocks, and wherein at least one of polymer blocks has been functionalized; and
  (2) a plurality of nanoparticles on the block copolymer, wherein the nanoparticles are dispersed on the block copolymer, and wherein the nanoparticles adhere to at least 90% of the block copolymer domains that have been functionalized;
(b) adhering an analyte to the nanoparticle array;
(c) exposing the analyte to incident light of an excitation wavelength that overlaps with the metallic nanoparticle plasmon resonance band; and
(d) detecting the presence of the analyte by monitoring the presence or absence of a known Raman spectrum for the analyte.

BRIEF DESCRIPTION OF DRAWINGS

The patent or application file contains at least one drawing executed in color. Copies of the patent or patent application publication with color drawing(s) will be provided by the Office upon request and payment of the necessary fee.

DETAILED DESCRIPTION OF THE INVENTION

Figure 1:
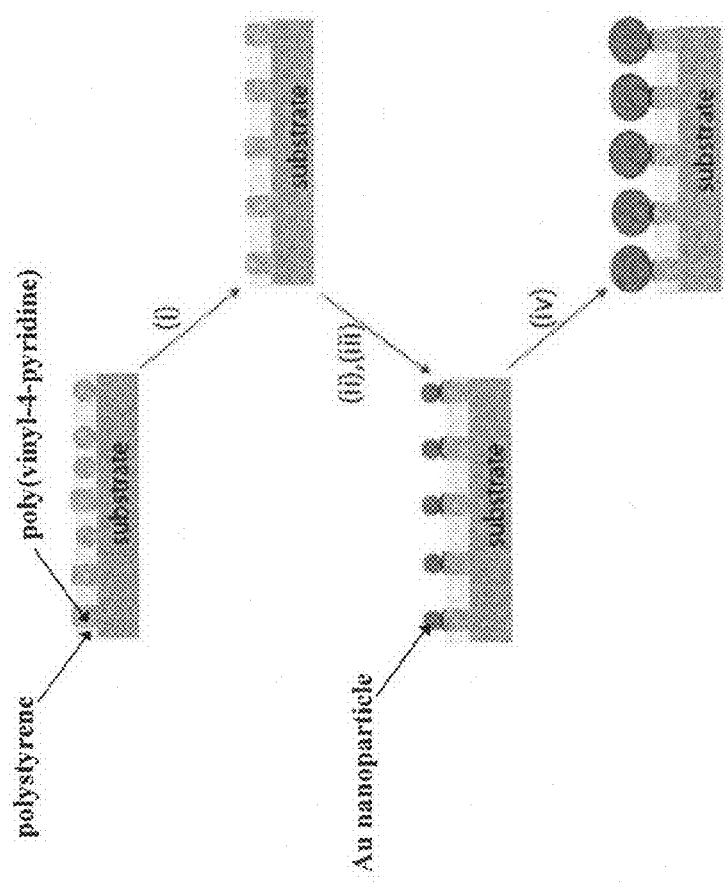
FIG. 1 is a scheme illustrating the surface-enhanced Raman scattering (SERS) substrate fabrication process of (i) solvent annealing; (ii) quaternization; (iii) colloid adsorption; and (iv) overgrowth.

In one embodiment, the disclosure provides a method of producing a nanoparticle array comprising:
(a) applying a block copolymer onto a substrate to give a thin film;
(b) reacting the applied block copolymer with an functionalizing agent;
(c) immersing the thin film in a nanoparticle suspension to give a nanoparticle array disposed on the thin film; and
(d) immersing the nanoparticle array in a growth solution;
wherein the nanoparticles are dispersed on the block copolymer.

Application of the Block Copolymer

As used herein, the term "polymer block" refers to a grouping of multiple monomer units of a single type (i.e., a homopolymer block) or multiple types (i.e., a copolymer block) of constitutional units into a continuous polymer chain.

As used herein, the term "block copolymer" refers to a polymer composed of chains where each chain contains two or more polymer blocks. A wide variety of block polymers are contemplated herein including diblock copolymers (i.e., polymers including two polymer blocks), triblock copolymers (i.e., polymers including three polymer blocks), multiblock copolymers (i.e., polymers including more than three polymer blocks), and combinations thereof.

In some embodiments, the block copolymer comprises at least one block of poly(9,9-bis(6'-N,N,Ntrimethylammonium)-hexyl)-fluorene phenylene) (PFP), polydimethylsiloxane (PDMS), poly(4-vinylpyridine) (P4VP), poly(-vinylpyridine), hydroxypropyl methylcellulose (HPMC), polyethylene glycol (PEG), poly(ethylene oxide)-co-poly(propylene oxide) di- or multiblock copolymers, poly(vinyl alcohol) (PVA), poly(ethylene-co-vinyl alcohol), poly(acrylic acid), poly(ethyloxazoline), a poly(alkylacrylate), poly(acrylamide), a poly(N-alkylacrylamide), a poly(N,N-dialkylacrylamide), poly(propylene glycol) (PPG), poly(propylene oxide), partially or fully hydrolyzed poly(vinyl alcohol), dextran, polystyrene (PS), polyethylene (PE), polypropylene (PP), polychloroprene (CR), a polyvinyl ether, poly(vinyl acetate) ($PV_{Ac}$), poly(vinyl chloride) (PVC), poly(isoprene), poly(ethylene), poly(butadiene), a polysiloxane, a polyurethane (PU), a polyacrylate, or a polyacrylamide.

The term "about," as used herein, includes the recited number ±10%. Thus, "about 10" means 9 to 11.

In some embodiments, the block copolymer comprises at least two polymer blocks (i.e., a first polymer block and a second polymer block) that are substantially immiscible in one another. In some embodiments, the block copolymer comprises a first polymer block and a second polymer block with a number average molecular weight ratio in a range of from about 5:95 to about 95:5, from about 5:95 to about 90:10, from about 5:95 to about 80:20, from about 5:95 to about 70:30, from about 5:95 to about 60:40, from about 5:95 to about 50:50, from about 5:95 to about 40:60, from about 5:95 to about 30:70, from about 5:95 to about 20:80, from about 5:95 to about 10:90, from about 10:90 to about 95:5, from about 10:90 to about 90:10, from about 10:90 to about 80:20, from about 10:90 to about 70:30, from about 10:90 to about 60:40, from about 10:90 to about 50:50, from about 10:90 to about 40:60, from about 10:90 to about 30:70, from about 10:90 to about 20:80, from about 20:80 to about 95:5, from about 20:80 to about 90:10, from about 20:80 to about 80:20, from about 20:80 to about 70:30, from about 20:80 to about 60:40, from about 20:80 to about 50:50, from about 20:80 to about 40:60, from about 20:80 to about 30:70, from about 30:70 to about 95:5, from about 30:70 to about 90:10, from about 30:70 to about 80:20, from about 30:70 to about 70:30, from about 30:70 to about 60:40, from about 30:70 to about 50:50, from about 30:70 to about 40:60, from about 40:60 to about 95:5, from about 40:60 to about 90:10, from about 40:60 to about 80:20, from about 40:60 to about 70:30, from about 40:60 to about 60:40, from about 40:60 to about 50:50, from about 50:50 to about 95:5, from about 50:50 to about 90:10, from about 50:50 to about 80:20, from about 50:50 to about 70:30, from about 50:50 to about 60:40, from about 60:40 to about 95:5, from about 60:40 to about 90:10, from about 60:40 to about 80:20, from about 60:40 to about 70:30, from about 70:30 to about 95:5, from about 70:30 to about 90:10, from about 70:30 to about 80:20, from about 80:20 to about 95:5, from about 80:20 to about 90:10, or from about 90:10 to about 95:5.

In some embodiments, the polymer block is a functionalized polymer block. A functionalized polymer block contains an organic functional group such as an amine, quaternary ammonium, hydroxyl, thiol, carboxylate, carboxylic acid, sulfate, sulfonate, sulfonic acid, epoxide, phosphate, or phosphonate.

In some embodiments, the block copolymer is polystyrene-block-poly(4-vinylpyridine) (PS-b-P4VP), polyisoprene-b-poly(4-vinylpyridine), polybutadiene-block-poly(4-vinylpyridine), polyethylene-block-poly(4-vinylpyridine), polystyrene-block-poly(2-vinylpyridine), polyisoprene-b-poly(2-vinylpyridine), polybutadiene-block-poly(2-vinylpyridine), or polyethylene-block-poly(2-vinylpyridine).

In some embodiments, the block copolymer is polystyrene-block-poly(4-vinylpyridine). In some embodiments, the number average molecular weight (kg/mol) of polystyrene to poly(4-vinylpyridine) is 50 to 13, 90 to 50, 109 to 30, 160 to 21, 196 to 122, 198 to 650, 230 to 48, 240 to 66, 270 to 137, 280 to 130, 300 to 175, 311 to 120, 342 to 53, 350 to 11.5, 575 to 141, 620 to 10, 700 to 35, 700 to 220, 710 to 225, 900 to 180, 925 to 310, 1000 to 298, 1100 to 285, 1270 to 57, 1300 to 76, 1500 to 15, 1700 to 40, 1800 to 410, 2500 to 40, 47 to 10, 47.5 to 15.5, 175 to 65, or 75 to 25. In some embodiments, the number average molecular weight (kg/mol) of polystyrene to poly(4-vinylpyridine) is 47 to 10. In some embodiments, the number average molecular weight (kg/mol) of polystyrene to poly(4-vinylpyridine) is 47.5 to 15.5. In some embodiments, the number average molecular weight (kg/mol) of polystyrene to poly(4-vinylpyridine) is 175 to 65. In some embodiments, the number average molecular weight (kg/mol) of polystyrene to poly(4-vinylpyridine) is 75 to 25.

In some embodiments, the block copolymer is polystyrene-block-poly(2-vinylpyridine). In some embodiments the number average molecular weight (kg/mol) of polystyrene to poly(2-vinylpyridine) is 32.5 to 12, 43 to 69, or 290 to 72.

As used herein, the term "thin film" refers to a layer of material deposited on a substrate that can range from fractions of a nanometer to several micrometers in thickness. In some embodiments, the thickness of the thin film is from about 0.01 nm to about 1000 nm, from about 0.01 nm to about 100 nm, from about 0.01 nm to about 50 nm, from about 1 nm to about 1000 nm, from about 1 nm to about 100 nm, from about 1 nm to about 50 nm, from about 5 nm to about 1000 nm, from about 5 nm to about 100 nm, or from about 5 nm to about 50 nm.

The block copolymer thin films described herein may be formed by any suitable technique including, but not limited to, spin-coating, blanket coating, dip coating, spray coating, ink-jet printing, microdroplet printing, additive manufacturing, chemical vapor deposition, or physical vapor deposition. In some embodiments, the thin films are formed by spin-coating.

As used herein, the term "substrate" refers to a material with sufficient load bearing capability and internal strength to withstand the application of additional layers of material. In some embodiments, the substrate is a metal, an alloy, a ceramic, a semiconductor, a plastic, a composite, a natural fiber, a synthetic fiber, glass, silicon, paper, wood, or quartz. In some embodiments, the substrate is steel or aluminum.

In some embodiments, the substrate is selected from the group consisting of a plastic, polymeric film, metal, silicon, glass, fabric, paper, and combinations thereof. In some embodiments, the substrate is glass. In some embodiments, the substrate is silicon.

In some embodiments, the substrate is a metallic film on a polymeric, glass, or ceramic substrate, a metallic film on a conductive film, films on a polymeric substrate, or a metallic film on a semiconducting film on a polymeric substrate. In some embodiments, the substrate is glass, indium-tin-oxide coated glass, indium-tin-oxide coated polymeric films; polyethylene terephthalate, polyethylene naphthalate, polyimides, silicon, or a metal foil.

In some embodiments, the substrate is non-planar. In some embodiments, the non-planar substrate is a spherical bead, a tube, a flask, a fiber, a wire, or a needle. In some embodiments, the substrate has a surface roughness larger than the thickness of the block copolymer film.

As used herein the term "annealing" refers to treatment of the block copolymer so as to enable sufficient microphase segregation between the two or more different polymeric block components of the block copolymer to form an ordered pattern defined by repeating structural units formed from the polymer blocks. Annealing of the block copolymer in the present invention may be achieved by various methods known in the art, including, but not limited to: thermal annealing (either in a vacuum or in an inert atmosphere, such as nitrogen or argon), solvent vapor-assisted annealing (either at or above room temperature), or supercritical fluid-assisted annealing. In some embodiments, thermal annealing of the block copolymer may be conducted by exposing the block copolymer to an elevated temperature that is above the glass transition temperature ($T_g$), but below the degradation temperature ($T_d$). Other conventional annealing methods not described herein may also be utilized.

In some embodiments, the annealing is by thermal annealing. In thermal annealing, the block copolymer is heated to an elevated temperature which is maintained for a period of time and then cooled. The cooling can be slow (i.e., in air) or quick (i.e. by quenching in water). In some embodiments, the block copolymer exposed to an elevated temperature of between about 50° C. to about 220° C., between about 50° C. to about 200° C., between about 50° C. to about 150° C., between about 50° C. to about 100° C., between about 50° C. to about 75° C., between about 75° C. to about 220° C., between about 75° C. to about 200° C., between about 75° C. to about 150° C., between about 75° C. to about 100° C., between about 100° C. to about 220° C., between about 100° C. to about 200° C., between about 100° C. to about 150° C., between about 150° C. to about 220° C., between about 150° C. to about 200° C., or between about 200° C. to about 220° C.

In some embodiments, the block copolymer is exposed to an elevated temperature for 10 seconds, 15 seconds, 20 seconds, 25 seconds, 30 seconds, 35 seconds, 40 seconds, 45 seconds, 50 seconds, 55 seconds, 1 minute, 5 minutes, 10 minutes, 20 minutes, 30 minutes, 1 hour, 6 hours, 12 hours, 1 day, 3 days, 1 week, or 2 weeks.

In some embodiments, the annealing is by solvent vapor annealing. In solvent vapor annealing, the deposited layers are exposed to solvent vapor. In some embodiments, the solvent is selected from the group consisting of acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme, 1,2-dimethoxy-ethane, dimethylether, dimethylformamide, dimethylsulfoxide, dioxane, ethanol, ethyl acetate, ethylene glycol, glycerin, heptane, hexamethylphosphoramide, hexamethylphosphorus triamide, hexane, methanol, methyl t-butyl ether, methylene chloride, N-methyl-2-pyrrolidinone, nitromethane, pentane, petroleum ether, 1-propanol, 2-propanol, propylene glycol methyl ether acetate (PGMEA), pyridine, tetrahydrofuran, toluene, triethyl amine, water, o-xylene, m-xylene, p-xylene, and combinations thereof. In some embodiments, the solvent is tetrahydrofuran. In some embodiments, the solvent is a combination of tetrahydrofuran and deionized water. In some embodiments, the solvent is a combination of tetrahydrofuran and deionized water in a volume ratio of 1:1. In some embodiments, the solvent is PGMEA.

In some embodiments, the solvent vapor annealing time is 10 seconds, 15 seconds, 20 seconds, 25 seconds, 30 seconds, 35 seconds, 40 seconds, 45 seconds, 50 seconds, 55 seconds, 1 minute, 5 minutes, 10 minutes, 20 minutes, 30 minutes, 1 hour, 6 hours, 12 hours, 1 day, 3 days, 1 week, or 2 weeks. In some embodiments, the solvent vapor annealing time is 30 seconds.

In some embodiments, the relative humidity (RH) is controlled during the spin-coating of the block copolymer onto the substrate. In some embodiments, the relative humidity is between about 5% and about 75%, between about 5% and about 60%, between about 5% and about 50%, between about 5% and about 40%, between about 5% and about 30%, between about 5% and about 20%, between about 5% and about 10%, between about 10% and about 75%, between about 10% and about 60%, between about 10% and about 50%, between about 10% and about 40%, between about 10% and about 30%, between about 10% and about 20%, between about 20% and about 75%, between about 20% and about 60%, between about 20% and about 50%, between about 20% and about 40%, between about 20% and about 30%, between about 30% and about 75%, between about 30% and about 60%, between about 30% and about 50%, between about 30% and about 40%, between about 40% and about 75%, between about 40% and about 60%, between about 40% and about 50%, between about 50% and about 75%, between about 50% and about 60%, or between about 60% and about 75%. In some embodiments, the relative humidity is about 23%. In some embodiments, the relative humidity is about 37%. In some embodiments, the relative humidity is about 50%.

The term "block copolymer domain" as used herein refers to a physical volume of the block copolymer film that consists mainly of one of the polymer blocks. The domains result from microphase separation because of the incompatibility between the polymer blocks. The domains arrange into a pattern. The pattern can be a regular or an irregular pattern. In some embodiments, the domain can be spherical, hemispherical, rod-like, cylindrical, sheet-like, planar, straight, or curved. The regular patterns can be hexagonal, triangular, square, rectangular, centered rectangular, cubic, face-centered cubic, body-centered cubic or lamellar. The regular patterns can show regularity in one, two, or three dimensions.

Functionalization

To improve the templating capabilities of the block copolymer thin film, the film is reacted with a functionalizing agent.

The term "functionalizing agent" as used herein refers to a chemical reagent that is used to modify the chemical composition of a polymer such that a desired functional group is covalently linked to the polymer at the end of the reaction. In some embodiments, the functionalizing agent is an alkylating agent, a cross-linking agent, a carboxylating agent, an oxidizing agent, a reducing agent, or an epoxidating agent. In some embodiments, the functionalizing agent is an alkyl halide, an aryl halide, an alkyl dihalide, an alkyl dialdehyde, or an alkyl diamine. In some embodiments, the functionalizing agent is glutaraldehyde, formic acid, chromic acid, sodium borohydride, sodium, 1,2-propylene oxide, glycidol, succinic anhydride, or succinimide.

Quaternary ammonium cations are positively charged polyatomic ions of the structure $NR_4^+$, R being an alkyl group or an aryl group. Quaternary ammonium compounds are prepared by alkylation of tertiary amines, in a process called quaternization.

In some embodiments, at least one of polymer blocks is quaternized by exposing the polymer block to an alkylating agent. In some embodiments, quaternary ammonium cations are introduced to at least one polymer block by reaction with cationic reagents, e.g., reacting nucleophilic moieties of the polymer block with QUAT-188 (Sajomsang, W., et al., *Carbohydrate Research* 344:2502 (2009)).

The term "alkylating agent" as used herein refers to a reagent capable of placing an alkyl group onto a nucleophilic site. In some embodiments, the alkylating agent is an organic halide, an organic dihalide, an alkyl sulfate, an alkyl disulfate, or an alkyl or aryl disulfonate. In some embodiments, the alkylating agent is an organic dihalide, e.g., an alkyl dihalide, such as 1,4-dibromobutane, 1,5-dibromopentane, 1,6-dibromohexane, 1,7-dibromoheptane, 1,8-dibromooctane, 1,9-dibromononane, 1,4-dichlorobutane, 1,5-dichloropentane, 1,6-dichlorohexane, 1,7-dichloroheptane, 1,8-dichlorooctane, 1,9-dichlorononane, and combinations thereof. In some embodiment, the alkylating agent is an aryl disulfonate, such as anthraquinone-2,6-disulfonate or 1,5-naphthalene disulfonate. In some embodiments, the alkylating agent is benzyl bromide or benzyl chloride. In some embodiments, the alkylating agent is 1,4-dibromobutane.

In some embodiments, the pyridine groups of the P4VP block are converted into quaternary pyridinium groups (as well as crosslinked) by exposing the film to 1,4-dibromobutane (DBB) vapor. There are two beneficial consequences to the reaction with DBB. First, the P4VP domains of the film become positively-charged. The quaternized P4VP domains selectively trap negatively-charged nanoparticles from suspension through electrostatic interactions—the nanoparticle immobilization process is highly localized and effectively irreversible due to the strength of the interaction. Second, each cylindrical P4VP domain of the film becomes crosslinked. This contributes to the stability of the self-assembly structure, reducing swelling and surface-reconstruction upon exposure to various solvents. The quaternization reaction provides a template to build upon a nanoparticle array that has a predictable periodicity and no detectable deterioration during preparation and use.

Colloid Adsorption

Immersion of the block polymer film into a nanoparticle suspension results in the self-assembly of the nanoparticles into an array commensurate with the array of the domains of the polymer. The self-assembly of the nanoparticles is driven by forces acting between specific polymer blocks and the nanoparticles, for example: electrostatic interaction between positively charges polymer blocks and negatively charges nanoparticles, electrostatic interactions between negatively charged polymer domains and positively charged nanoparticles, chemical affinity between functional groups in the polymer block and the surface of the nanoparticle, hydrogen bonding between functional groups in the polymer block and surfactants on the nanoparticle, or hydrophobic interactions between the polymer block and the nanoparticle. As used herein, the term "adsorption" refers to the accumulation of nanoparticles on the surface of the thin film.

As used herein, the term "nanoparticle" refers to solid particles whose size is typically measured in nanometers. In some embodiments, the nanoparticles used in connection with the present invention may have a mean diameter of 100 nanometers or less. In some embodiments, the diameter of the nanoparticle is between about 5 nm and about 100 nm, between about 5 nm and about 80 nm, between about 5 nm and about 60 nm, between about 5 nm and about 40 nm, between about 5 nm and about 20 nm, between about 5 nm and about 10 nm, between about 10 nm and about 100 nm, between about 10 nm and about 80 nm, between about 10 nm and about 60 nm, between about 10 nm and about 40 nm, between about 10 nm and about 20 nm, between about 20 nm and about 100 nm, between about 20 nm and about 80 nm, between about 20 nm and about 60 nm, between about 20 nm and about 40 nm, between about 40 nm and about 100 nm, between about 40 nm and about 80 nm, between about 40 nm and about 60 nm, between about 60 nm and about 100 nm, between about 60 nm and about 80 nm, or between about 80 nm and about 100 nm. In some embodiments, the diameter of the nanoparticle is 15 nm. In some embodiments, the diameter of the nanoparticle is 20 nm. In some embodiments, the diameter of the nanoparticle is 30 nm.

The nanoparticles used in conjunction with the present invention may include a core of atoms that form inorganic conductors, dielectrics, or semiconductors. In some embodiments, the atoms form oxides, nitrides, sulfides, and semiconductor compounds. Because of their ultra-small size, the nanoparticles may impart novel mechanical, optical, electrical, and magnetic properties to materials, devices, and systems that are assembled from them. In some embodiments, suitable materials for fabrication of the nanoparticles are Au, Ag, Cu, Li, Pt, silica, alumina, titania, magnetite, or FePt.

In some embodiments, the nanoparticle is a quantum dot, a magnetic nanoparticle, an oxide nanoparticle, or a nanoparticle carrying negatively charged surface groups (carboxylates, borates, etc.). Specific examples of such quantum dots include, but are not limited to, those comprising materials including CdS, CdSe, CdTe, ZnS, ZnSe, ZnTe, GaN, GaP, GaAs, GaSb, AlN, AlP, AlAs, AlSb, InP, InAs, and InSb. Where quantum dots having a core-shell structure are used, the core may be overcoated with a material selected from the group consisting of ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, Au, Ag, Cu, Co, Ni, Pt, Pd, and mixtures thereof.

In some embodiments, the nanoparticles are coated with organic or polymer surfactants.

In some embodiments, the thin film is immersed in a nanoparticle suspension for a sufficient time to attach nanoparticles to 100%, 99%, 98%, 97%, 96%, 95%, 94%, 93%, 92%, 91%, or 90% of the block copolymer domains that have been functionalized. In some embodiments, the thin film is immersed in the nanoparticle suspension for between 3 seconds and 6 hours, between 3 seconds and 3 hours, between 3 seconds and 1 hour, between 3 seconds and 50 minutes, between 3 seconds and 40 minutes, between 3 seconds and 30 minutes, between 3 seconds and 20 minutes, between 3 seconds and 15 minutes, between 3 seconds and 10 minutes, between 3 seconds and 7 minutes, between 3 seconds and 5 minutes, between 3 seconds and 3 minutes, between 3 seconds and 1 minute, between 1 minute and 6 hours, between 1 minute and 3 hours, between 1 minute and 1 hour, between 1 minute and 50 minutes, between 1 minute and 40 minutes, between 1 minute and 30 minutes, between 1 minute and 20 minutes, between 1 minute and 15 minutes, between 1 minute and 10 minutes, between 1 minute and 7 minutes, between 1 minute and 5 minutes, between 1 minute and 3 minutes, between 3 minutes and 6 hours, between 3 minutes and 3 hours, between 3 minutes and 1 hour, between 3 minutes and 50 minutes, between 3 minutes and 40 minutes, between 3 minutes and 30 minutes, between 3 minutes and 20 minutes, between 3 minutes and 15 minutes, between 3 minutes and 10 minutes, between 3 minutes and 7 minutes, between 3 minutes and 5 minutes, between 5 minutes and 6 hours, between 5 minutes and 3 hours, between 5 minutes and 1 hour, between 5 minutes and 50 minutes, between 5 minutes and 40 minutes, between 5 minutes and 30 minutes, between 5 minutes and 20 minutes, between 5 minutes and 15 minutes, between 5 minutes and 10 minutes, between 5 minutes and 7 minutes, between 7 minutes and 6 hours, between 7 minutes and 3 hours, between 7 minutes and 1 hour, between 7 minutes and 50 minutes, between 7 minutes and 40 minutes, between 7 minutes and 30 minutes, between 7 minutes and 20 minutes, between 7 minutes and 15 minutes, between 7 minutes and 10 minutes, between 10 minutes and 6 hours, between 10 minutes and 3 hours, between 10 minutes and 1 hour, between 10 minutes and 50 minutes, between 10 minutes and 40 minutes, between 10 minutes and 30 minutes, between 10 minutes and 20 minutes, between 10 minutes and 15 minutes, between 15 minutes and 6 hours, between 15 minutes and 3 hours, between 15 minutes and 1 hour, between 15 minutes and 50 minutes, between 15 minutes and 40 minutes, between 15 minutes and 30 minutes, between 15 minutes and 20 minutes, between 20 minutes and 6 hours, between 20 minutes and 3 hours, between 20 minutes and 1 hour, between 20 minutes and 50 minutes, between 20 minutes and 40 minutes, between 20 minutes and 30 minutes, between 30 minutes and 6 hours, between 30 minutes and 3 hours, between 30 minutes and 1 hour, between 30 minutes and 50 minutes, between 30 minutes and 40 minutes, between 40 minutes and 6 hours, between 40 minutes and 3 hours, between 40 minutes and 1 hour, between 40 minutes and 50 minutes, between 50 minutes and 6 hours, between 50 minutes and 3 hours, between 50 minutes and 1 hour, between 1 hour and 6 hours, between 1 hour and 3 hours, or between 3 hours and 6 hours.

In some embodiments, the adsorption of the nanoparticles is selective to one type of polymer block (e.g. nanoparticles adsorb to at least 90% of the domains of one of the polymer blocks and no more that 10% of the domains of other polymer blocks).

In some embodiments, one type of nanoparticle is adsorbed to block copolymer domains that have been functionalized by one type of functionalization agent and a second type of nanoparticles is adsorbed to block copolymer domains that have been functionalized by a second type of functionalization agent.

In some embodiments, the block copolymer domain is in contact with one nanoparticle. In some embodiments, the block copolymer domains is in contact with multiple nanoparticles.

In one embodiment, the nanoparticle array is formed to a high density of approximately $1 \times 10^9$ nanoparticles/cm$^2$, $1 \times 10^{10}$ nanoparticles/cm$^2$, $1 \times 10^{11}$ nanoparticles/cm$^2$, $2 \times 10^{11}$ nanoparticles/cm$^2$, $5 \times 10^{11}$ nanoparticles/cm$^2$, $1 \times 10^{12}$ nanoparticles/cm$^2$, or $2 \times 10^{12}$ nanoparticles/cm$^2$. In some embodiments, the nanoparticle array is substantially free of voids or defects (e.g., missing a particle, containing two nanoparticles). As used herein, "substantially free of" means that the number of voids present, if any, are sufficiently few in number such that any such voids would not significantly adversely affect the desired properties of the nanoparticle array. As used herein, "substantially free of" refers to less than about 50 defects/$\mu m^2$. In another embodiment, the nanoparticle array has less than about 40 defects/$\mu m^2$, less than about 30 defects/$\mu m^2$, less than about 20 defects/$\mu m^2$, less than about 15 defects/$\mu m^2$, less than about 15 defects/$\mu m^2$, less than about 10 defects/$\mu m^2$, less than about 9 defects/$\mu m^2$, less than about 8 defects/$\mu m^2$, less than about 7 defects/$\mu m^2$, less than about 6 defects/$\mu m^2$, less than about 5 defects/$\mu m^2$, or less than about 4 defects/$\mu m^2$.

Overgrowth

The gap between adjacent nanoparticles is a major factor that determines the surface plasmon resonance frequency and the SERS enhancement factor. The inter-particle gap size is the difference between the center-to-center spacing (set by the block-copolymer template) and the nanosphere diameter. The gap size can be tuned by metal overgrowth over the nanoparticles anchored on the surface by immersing the thin film in a growth solution.

In some embodiments, the gap size can be controlled. In some embodiments, the gap size is between about 0.5 nm and about 1000 nm, between about 0.5 nm and about 100 nm, between about 0.5 nm and about 50 nm, between about 0.5 nm and about 10 nm, between about 0.5 nm and about 1 nm, between about 1 nm and about 1000 nm, between about 1 nm and about 100 nm, between about 1 nm and about 50 nm, between about 1 nm and about 10 nm, between about 10 nm and about 1000 nm, between about 10 nm and about 100 nm, between about 10 nm and about 50 nm, between about 100 and about 1000 nm.

In some embodiments, the growth solution is a metal growth solution. In some embodiments, the growth solution is a non-metal growth solution.

In some embodiments, the metal growth solution comprises a metal atom selected from the group consisting of Au, Ag, Cu, Li, Fe, Co, Ni, and Pt. In some embodiments, the metal growth solution comprises the metal atom Au or Ag. In some embodiments, the metal growth solution comprises the metal atom Au. In some embodiments, the metal growth solution comprises the metal atom Ag.

In some embodiments, the non-metal growth solution comprises precursors to non-metals. In some embodiments, the non-metal is $SiO_2$, $TiO_2$, $Fe_2O_3$, $Al_2O_3$, CdS, CdSe, PbS, PbSe, or $Bi_2S_3$. In some embodiments, the precursor is an organometallic compound, a metal alkoxide, silicon tetrachloride, tetra ethoxysilane, a metal salt, sulfur, selenium, sodium sulfide, sodium selenide, triphenylphosphine selenide, or triphenylphosphine telluride.

In some embodiments, the thin film is immersed in a growth solution for a sufficient time to increase the average diameter of the nanoparticles and to decrease the gap between adjacent nanoparticles (to approximately 1 nm). In some embodiments, the thin film is immersed in the metal growth solution for between 30 seconds and 72 hours, 30 seconds and 48 hours, 30 seconds and 24 hours, 30 seconds and 12 hours, between 30 seconds and 6 hours, between 30 seconds and 3 hours, between 30 seconds and 1 hour, between 30 seconds and 50 minutes, between 30 seconds and 40 minutes, between 30 seconds and 30 minutes, between 30 seconds and 20 minutes, between 30 seconds and 15 minutes, between 30 seconds and 10 minutes, between 30 seconds and 7 minutes, between 30 seconds and 5 minutes, between 30 seconds and 3 minutes, between 30 seconds and 1 minute, between 1 minute and 72 hours, between 1 minute and 48 hours, between 1 minute and 24 hours, between 1 minute and 12 hours, between 1 minute and 6 hours, between 1 minute and 3 hours, between 1 minute and 1 hour, between 1 minute and 50 minutes, between 1 minute and 40 minutes, between 1 minute and 30 minutes, between 1 minute and 20 minutes, between 1 minute and 15 minutes, between 1 minute and 10 minutes, between 1 minute and 7 minutes, between 1 minute and 5 minutes, between 1 minute and 3 minutes, between 3 minutes and 72 hours, between 3 minutes and 48 hours, between 3 minutes and 24 hours, between 3 minutes and 12 hours, between 3 minutes and 6 hours, between 3 minutes and 3 hours, between 3 minutes and 1 hour, between 3 minutes and 50 minutes, between 3 minutes and 40 minutes, between 3 minutes and 30 minutes, between 3 minutes and 20 minutes, between 3 minutes and 15 minutes, between 3 minutes and 10 minutes, between 3 minutes and 7 minutes, between 3 minutes and 5 minutes, between 5 minutes and 72 hours, between 5 minutes and 48 hours, between 5 minutes and 24 hours, between 5 minutes and 12 hours, between 5 minutes and 6 hours, between 5 minutes and 3 hours, between 5 minutes and 1 hour, between 5 minutes and 50 minutes, between 5 minutes and 40 minutes, between 5 minutes and 30 minutes, between 5 minutes and 20 minutes, between 5 minutes and 15 minutes, between 5 minutes and 10 minutes, between 5 minutes and 7 minutes, between 7 minutes and 72 hours, between 7 minutes and 48 hours, between 7 minutes and 24 hours, between 7 minutes and 12 hours, between 7 minutes and 6 hours, between 7 minutes and 3 hours, between 7 minutes and 1 hour, between 7 minutes and 50 minutes, between 7 minutes and 40 minutes, between 7 minutes and 30 minutes, between 7 minutes and 20 minutes, between 7 minutes and 15 minutes, between 7 minutes and 10 minutes, between 10 minutes and 6 hours, between 10 minutes and 3 hours, between 10 minutes and 1 hour, between 10 minutes and 50 minutes, between 10 minutes and 40 minutes, between 10 minutes and 30 minutes, between 10 minutes and 20 minutes, between 10 minutes and 15 minutes, between 15 minutes and 6 hours, between 15 minutes and 3 hours, between 15 minutes and 1 hour, between 15 minutes and 50 minutes, between 15 minutes and 40 minutes, between 15 minutes and 30 minutes, between 15 minutes and 20 minutes, between 20 minutes and 6 hours, between 20 minutes and 3 hours, between 20 minutes and 1 hour, between 20 minutes and 50 minutes, between 20 minutes and 40 minutes, between 20 minutes and 30 minutes, between 30 minutes and 6 hours, between 30 minutes and 3 hours, between 30 minutes and 1 hour, between 30 minutes and 50 minutes, between 30 minutes and 40 minutes, between 40 minutes and 6 hours, between 40 minutes and 3 hours, between 40 minutes and 1 hour, between 40 minutes and 50 minutes, between 50 minutes and 6 hours, between 50 minutes and 3 hours, between 50 minutes and 1 hour, between 1 hour and 6 hours, between 1 hour and 3 hours, or between 3 hours and 6 hours.

In some embodiments, the present invention provides a method for enhancing a Raman signal of an analyte comprising:

(a) providing a nanoparticle array comprising:
  (1) a block copolymer applied to a substrate, wherein the block copolymer comprises at least two polymer blocks, and wherein at least one of polymer blocks has been functionalized; and
  (2) a plurality of nanoparticles on the block copolymer, wherein the nanoparticles are dispersed on the block copolymer, and wherein the nanoparticles adhere to at least 90% of the block copolymer domains that have been functionalized;
(b) adhering an analyte to the nanoparticle array;
(c) exposing the analyte to incident light of an excitation wavelength that overlaps with the metallic nanoparticle plasmon resonance band; and
(d) detecting the optical signal of the analyte as Raman scattered radiation;

wherein the optical signal of the analyte is enhanced compared to the signal when the analyte is exposed to incident light in the absence of the nanoparticle array.

As used herein, the term "adhered" refers to the nanoparticle or the analyte being associated with a surface. In some embodiments, the nanoparticle or the analyte is chemically bonded to the surface by, for example, at least one covalent bond, ionic bond, coordination bond, or hydrogen bond. In some embodiments, the nanoparticle or the analyte is attracted to the surface by, for example, hydrophobic interactions or hydrophilic interactions. In some embodiments, the nanoparticle or the analyte is reversibly associated with the surface. In some embodiments, the nanoparticle or the analyte is placed in close proximity to the surface by limiting its diffusion using a restricting physical or chemical barrier.

In some embodiments, the analyte is a molecule. If the analyte is a molecule, it can be neutral, positively charged, negatively charged, or amphoteric. The analyte can be a solid, liquid or gas. Any species or collection of species that gives rise to a unique Raman spectrum, whether solid, liquid, gas, or a combination thereof, can serve as the analyte. In some embodiments, the analyte is dimethylformamide, thiocyanate, polypyrrole, hemoglobin, oligonucleotides, charcoal, diamond, grahene, graphite, carbon nanotubes, sulfur, polyacrylamide, citric acid, glucose, caffeine, cocaine, rhodamine 6g, or trans-1,2-bi-(4-pyridyl)ethylene.

In some embodiments, the analyte comprises a thiol moiety, a carboxylic acid moiety, an amine moiety, a pyridyl moiety, or a combination thereof. In some embodiments, the analyte comprises 4-mercaptobenzoic acid (4-MBA) or a derivative or salt thereof. In some embodiments, the analyte is 4-aminobenzenethiol.

In some embodiments, use of the methods and compositions of the invention results in enhancement of a Raman signal. The amount of enhancement can be referred to as an enhancement factor (EF). The EF can be expressed relative to an analyte in solution or an analyte on a surface. In one aspect, the SERS substrate has an enhancement factor of from about $10^3$ to about $10^9$ relative to the analyte in solution.

In some embodiments, the nanoparticle array is used for surface-enhanced Raman scattering, surface-enhanced infrared absorption, surface-enhanced fluorescence, surface-enhanced Raman optical activity, or surface-enhanced circular dichroism. In some embodiments, the nanoparticle array is used as a magnetic media substrate.

Raman Spectroscopy and Surface-Enhanced Raman Scattering (SERS)

In some embodiments, the nanoparticle array is used in SERS.

When light is directed onto a surface of assembled particles, the incident photons are absorbed, reflected and scattered differently depending on various properties of the particles including the elemental makeup, size, morphology, and spatial orientation. These optical properties have been extensively studied using various optical spectroscopies including infrared spectroscopy, Raman spectroscopy, fluorescence spectroscopy and reflectivity. The ability to tune the optical properties of surfaces using rational assembly of particles has broad applications in positive identification of targets of interest.

Raman spectroscopy is a branch of vibrational spectroscopy in which the transitions between vibrational states are studied using the scattered radiation produced when a molecule or a particle interacts with a photon of light. When laser light collides with a molecule, most of the incident photons are elastically scattered with no change in frequency. The Raman effect occurs from the very small fraction of incident photons (e.g., ~1 in every $10^7$ photons) that couple to distinct vibrational modes of the molecule, resulting in inelastically scattered radiation with a change in frequency. The energy difference between the inelastic scattered radiation and the incident light corresponds to the energy involved in changing the molecule's vibrational state. Plotting the intensity of this energy change verses the related frequency shift gives the Raman spectrum.

The Raman effect can be significantly enhanced by localizing molecules close to nanostructured noble metal surfaces (e.g., copper, silver, or gold). Typical enhancement factors are on the order of $10^6$ (Kneipp, K., et al., *Chem Rev* 99:2957 (1999)), and under appropriate conditions single molecule detection has been achieved (S. Nie and S. R. Emory, *Science* 275:1102 (1997)). The process is called surface-enhanced Raman scattering (SERS). The SERS effect is limited to a fairly narrow range of molecules that can make close contact with the noble metal surface (e.g., ≤50 Å). Nevertheless, this "limitation" can often be used to advantage in SERS-based analyses, that is, given the insensitivity of traditional Raman spectroscopy, analytes that are not localized near the noble metal surface are in a sense "invisible." Combining this with the fact that air and water (and other complex sample matrices) are transparent in Raman makes for a very powerful detection platform. Furthermore, given the fact that a typical Raman (or SERS) spectrum ranges from 200 and 3500 cm$^{-1}$ and Raman bands of many molecules are extremely narrow (e.g., 10-20 cm$^{-1}$), many different molecules can be detected simultaneously.

Surface Enhanced Infrared Absorption (SEIRA) Spectroscopy

In some embodiments, the nanoparticle array is used in SEIRA spectroscopy.

Similar to SERS, dramatic changes in the optical properties of molecules adsorbed on or near structured metal surfaces can also be observed using infrared spectroscopy. Surface enhanced infrared absorption (SEIRA) spectroscopy can be observed by direct mid-IR excitation of molecules that are localized close to roughened metal surfaces (e.g., molecules positioned at least ~8 nm from e.g., gold and silver nanoparticles or metal island films) (Hartstein, A., et al., *Phys. Rev. Lett.* 45: 201 (1980)). Specifically, direct mid-IR excitation of molecules can result in enhancement of vibrational bands that experience a change in dipole moment that is perpendicular to the roughened metal surface (Osawa, M., et al., *Appl. Spectrosc.* 47:1497 (1993)).

Typically this enhancement is approximately $10^1$-$10^3$, which is much more modest than SERS enhancements, but can reveal complementary information to SERS with respect to molecular structure and can be controlled by proper orientation of the molecule to the surface.

Surface Enhanced Fluorescence (SEF)

In some embodiments, the nanoparticle array is used in SEF.

Surface enhanced fluorescence (SEF) (also termed metal enhanced fluorescence or MEF) is the term for the phenomenon of the dramatic increase observed in the fluorescence emission when molecules are between ~3 nm and 60 nm from the surface of metals (e.g., silver and gold nanoparticles or island films) (Malicka, J., et al., *Anal. Biochem.* 315:57 (2003)). Thus, SERS or SEIRA effects have different distance dependency on the nanostructured surface than does the SEF effect (Champion, A., et al., *Chem. Phys. Lett.* 73:447 (1980)). SEF requires the molecule to be a certain distance from the metal surface to prevent fluorescence quenching due to nonradiative energy transfer from the excited state of the molecule to the metal. The SEF phenomenon arises from the interaction of the dipole moment of the fluorophore and the surface plasmon of the metal. This interaction can lead to an increase in radiative decay and an increase in fluorescence efficiency (Lakowicz, J. R., et al., *Anal. Biochem.* 301: 261-277 (2002)). Thus, even weakly emitting molecules having low quantum yields can be transformed into more efficient fluorophores when properly adsorbed to SEF-active surfaces (i.e., between 3-60 nm from the metal surface).

The following examples are illustrative and non-limiting of the nanoparticle arrays, methods of making, and methods of using described herein. Suitable modifications and adaptations of the variety of conditions, formulations and other parameters normally encountered in the field and which are obvious to those skilled in the art in view of this disclosure are within the spirit and scope of the invention.

EXAMPLES

Example 1

PS-b-P4VP block copolymer (number average molecular weight of polystyrene=47 kgmol$^{-1}$, number average molecular weight of poly(4-vinylpyridine)=10 kgmol$^{-1}$, polydispersity index=1.1) was purchased from Polymer Source, Inc. (Montreal, Canada) and used without further purification. Hexadecyl-trimethyl-ammonium bromide (CTAB), ascorbic acid, tetrahydrofuran (THF), and 1,4-dibromobutane (DBB) were purchased from Sigma-Aldrich (St. Louis, Mo.). Citrate-capped gold colloidal solution with a 15 nm mean diameter was purchased from BBInternational (Cardiff, United Kingdom). Silver nitrate (AgNO$_3$) and hydrogen tetrachloroaurate(III) trihydrate (HAuCl$_4$.3H$_2$O) were purchased from Alfa Aesar (Ward Hill, Mass.).

PS-b-P4VP block copolymer was dissolved in THF to yield a 0.5 wt % polymer solution. The polymer solution was prefiltered through a Millipore 0.45 µm poly(tetrafluoroethylene) filter. PS-b-P4VP films were prepared by spin-coating at 3000 rpm for 30 seconds on silicon or glass substrates at ~23% relative humidity (RH). As-spun films were annealed in THF at room temperature. The P4VP blocks in the PS-b-P4VP film were quaternized in DBB vapor. The PS-b-P4VP films were immersed in nanoparticle suspensions for 3 hours.

Gold growth solutions were prepared by mixing 6 mL of 0.2 M CTAB, 0.384 mL of 0.04 M HAuCl$_4$, 0.228 mL of 0.01 M AgNO$_3$, 0.96 mL of 0.1 M ascorbic acid, and 11 mL of deionized water.

Thin film surface morphology was characterized using a Dimension 3000 AFM from Digital Instruments, Inc (Tonawanda, N.Y.). Silicon tips on a cantilever with spring constants ranging between 20.0 and 80.0 Nm (as specified by the manufacturer) were used. The degree of quaternization was measured using X-ray photoelectron spectroscopy (XPS) on a Kratos AXIS 165 X-ray photoelectron spectrometer using a monochromatic Al Kα X-ray source (1486.6 eV). SEM observations were conducted using a Hitachi SU-70 Schottky FE-SEM working at 10 kV accelerating voltage and working distance around 5.5 mm. UV/Vis absorption spectra of the gold nanoparticle array films on glass substrates were measured using a Perkin-Elmer Lambda 25 UV/Vis spectrometer. The substrates were immersed in 0.4 mM 4-aminobenzenethiol (ABT) solution in ethanol for 3 hours, rinsed extensively with ethanol, and dried under nitrogen. Surface-enhanced Raman scattering (SERS) spectra were measured with a Horiba Jobin-Yvon LabRAM HR-VIS micro-Raman spectrometer equipped with 515 nm, 633 nm, and 785 nm laser sources, a confocal microscope, and an x-y scanning stage. A 50× objective (numerical aperture (NA)=0.5) was used for all the measurements. SERS spectra were obtained with incident laser power of 0.18 mW (515 nm), 0.11 mW (633 nm), and 0.06 mW (785 nm) and acquisition time of 30 seconds for all. The Raman spectra from a reference solution of 1.0 M 4-ABT in pentanediol was acquired. The integrated peak area values for the carbon-sulfur bond stretch of 4-ABT at 1078 cm$^{-1}$ were compared to get the SERS enhancement factor values.

Figure 2:
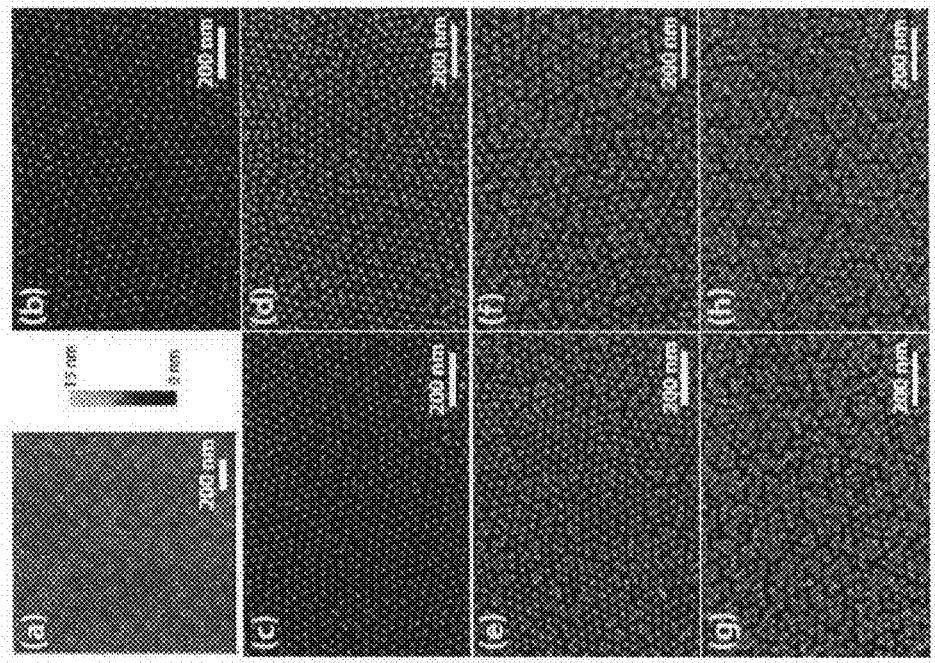
FIG. 2 is a series of eight images showing: (a) an atomic force microscope (AFM) image of the tetrahydrofuran (THF) annealed polystyrene-b-poly(vinyl-4-pyridine) (PS-b-P4VP) ordered film and scanning electron microscope (SEM) images of gold nanoparticle arrays of the quaternized PS-b-P4VP films after (b) 0 minutes; (c) 1 minute; (d) 3 minutes; (e) 5 minutes; (f) 7 minutes; (g) 10 minutes; and (h) 15 minutes.

As shown in FIG. 2, the SERS substrates consist of hexagonal arrays of metallic nanospheres with controllable diameters and lattice spacing. By controlling the size and the spacing between the nanospheres, tunable, tailored plasmonic response is achieved (Genov, D. A., et al., *Nano Lett.* 4:153 (2003); Jensen, T. R., et al., *J. Phys. Chem. B* 104:10549 (2000)).

As shown in FIG. 1, the underlying template for ordering the metallic nanospheres for the SERS substrates is formed through the self-assembly of a thin film of the block copolymer PS-b-P4VP. As the polymer solution is spin-cast and the solvent evaporates, the low solubility of the blocks in each other leads to segregation of the blocks into hydrophilic and hydrophobic domains of nanometer dimensions and long range order (Bates, F. S., et al., *Annu. Rev. Phys. Chem.* 41:525 (1990)) resulting in cylindrical domains of P4VP in a matrix of PS. Following a solvent-annealing step, the P4VP domains become more regularly-spaced and aligned perpendicular to the substrate (Kim, S. H., et al., *Adv. Mater.* 16:226 (2004)).

Figure 8:
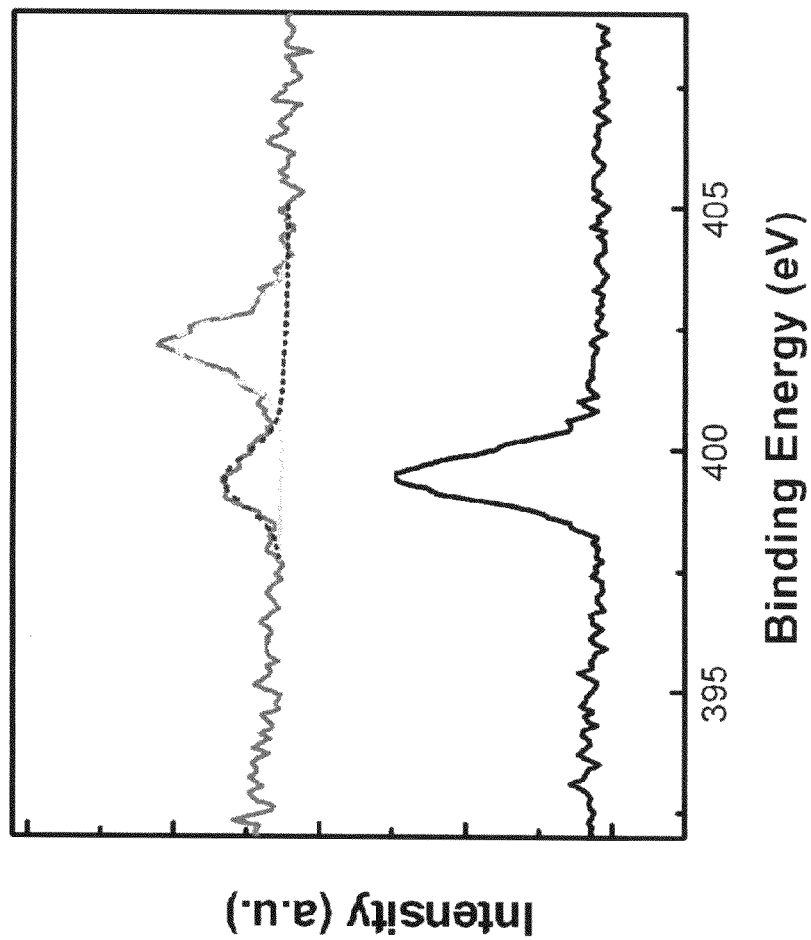
FIG. 8 is an X-ray photoelectron spectra (XPS) of the PS-b-P4VP film before (black dotted line) and after (grey dotted line) quaternization. The peak at 399.4 eV is attributable to the nitrogen in the pyridine group. After quaternization, an additional peak appears at a binding energy above 402 eV which is attributable to the positively-charged nitrogen.

As shown in FIG. 2a, the local environment around the domains has hexagonal symmetry and the long range order extends on the order of ~800 nanometers. The elevated P4VP domains are approximately 20 nm in diameter and the hexagonal lattice parameter is 42 nm. The center-to-center spacing and the diameter of the P4VP columns are controlled by the choice of the molecular weight of the polymers and the ratio between the number of 4-vinyl pyridine and styrene repeat units. To improve the templating capabilities of the block copolymer film, the pyridine groups of the P4VP block were converted into quaternary pyridinium groups (as well as crosslinked) by exposing the film to DBB vapor (Lam, Y. M., et al., *J. Colloid Interface Sci.* 317:255 (2008)). As shown in FIG. 8, XPS analysis of the quaternized films indicated a 66% conversion to the pyridinium bromide.

As shown in FIG. 2b, immersion of the quaternized block copolymer film in a suspension of citrate-stabilized gold nanospheres resulted in the self-assembly of the nanospheres into a hexagonal array commensurate with the array of P4VP domains. The adsorption of the gold nanospheres was complete within 3 hours, when 97% of the P4VP domains was covered by particles. As shown in FIG. 2b, the best ordering is achieved when the diameter of the gold nanospheres is slightly larger than the diameter of the P4VP domains, preventing the deposition of 2 gold nanospheres on a single P4VP domain. The templating is driven strictly by electrostatic interactions between the positively charged pyridinium groups on the substrate and the negatively charged surface ligands of the nanoparticles.

The gap between adjacent nanoparticles is a major factor that determines the surface plasmon resonance frequency and the SERS enhancement factor ((Genov, D. A., et al., *Nano Lett.* 4:153 (2003); Jensen, T. R., et al., *J. Phys. Chem. B* 104:10549 (2000); McMahon, J. M., et al., *Anal. Bioanal. Chem.* 394:1819 (2009); Wang, H. H., et al., *Adv. Mater.* 18:491 (2006); Jain, P. K., et al., *Nano Lett.* 7:2080 (2007); Farcau, C., et al., *J. Phys. Chem.* 114:11717 (2010)). The inter-particle gap size is the difference between the center-to-center spacing (set by the block-copolymer template) and the nanosphere diameter. The gap size was tuned by metal overgrowth over the nanoparticles anchored on the surface. As shown in FIGS. 2b-h and Table 1, soaking the substrate in an aqueous solution of HAuCl$_4$, silver nitrate, ascorbic acid, and hexadecyltrimethylammonium bromide ("Au growth solution") (Sau, T. S., et al., *Langmuir* 20:6414 (2004)) resulted in a gradual increase in nanosphere diameter and a concomitant reduction of the gap.

TABLE 1

Evolution of the parameters of the nanoparticle arrays as a function of time.

| Reaction time (min) | NP diameter (average ± standard dev) (nm)$^a$ | Gap size (calculated average) (nm)$^b$ |
|---|---|---|
| 0 | 16.6 ± 1.8 | 23.0 |
| 1 | 20.2 ± 1.5 | 18.4 |
| 3 | 24.8 ± 2.0 | 14.6 |
| 5 | 27.6 ± 2.4 | 11.2 |
| 7 | 32.7 ± 3.3 | 9.5 |
| 10 | 34.3 ± 4.4 | 6.6 |
| 15 | 36.5 ± 6.3 | 4.1 |

$^a$Analysis based on ~700 nanoparticles imaged by SEM in an area of 1.4 μm$^2$.
$^b$Calculated assuming a hexagonal lattice.

Figure 3:
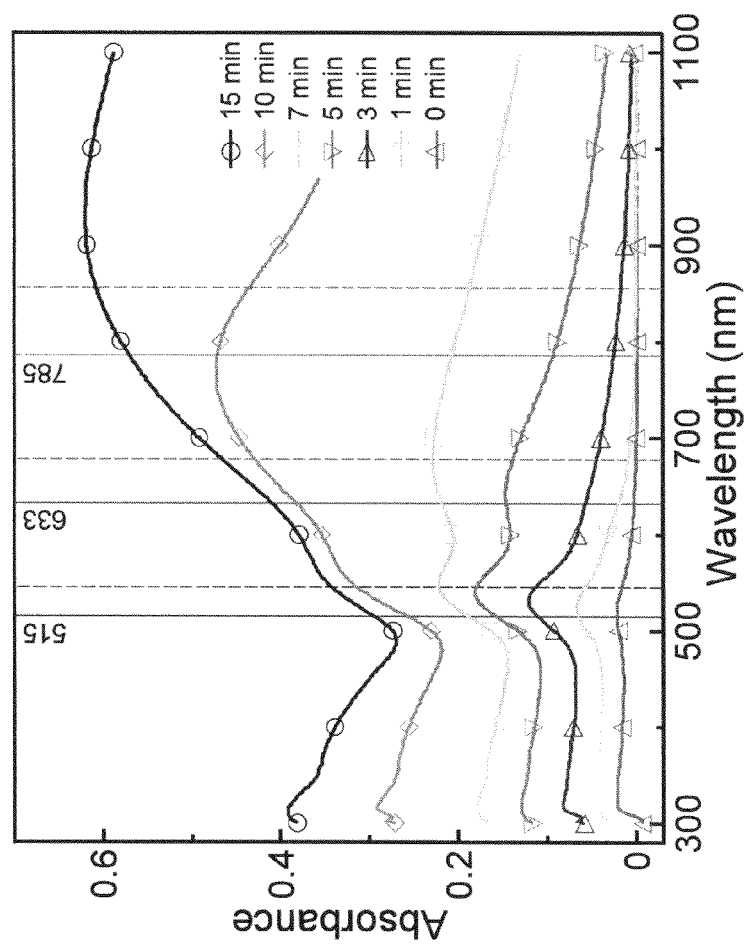
FIG. 3 is an ultraviolet-visible-infrared (UV-vis-NIR) attenuation spectra of SERS substrates fabricated on glass with overgrowth times ranging from 0 to 15 minutes. The vertical lines indicate the wavelengths of the incident (solid) and the scattered (dashed) light utilized in the SERS measurements.
Figure 4:
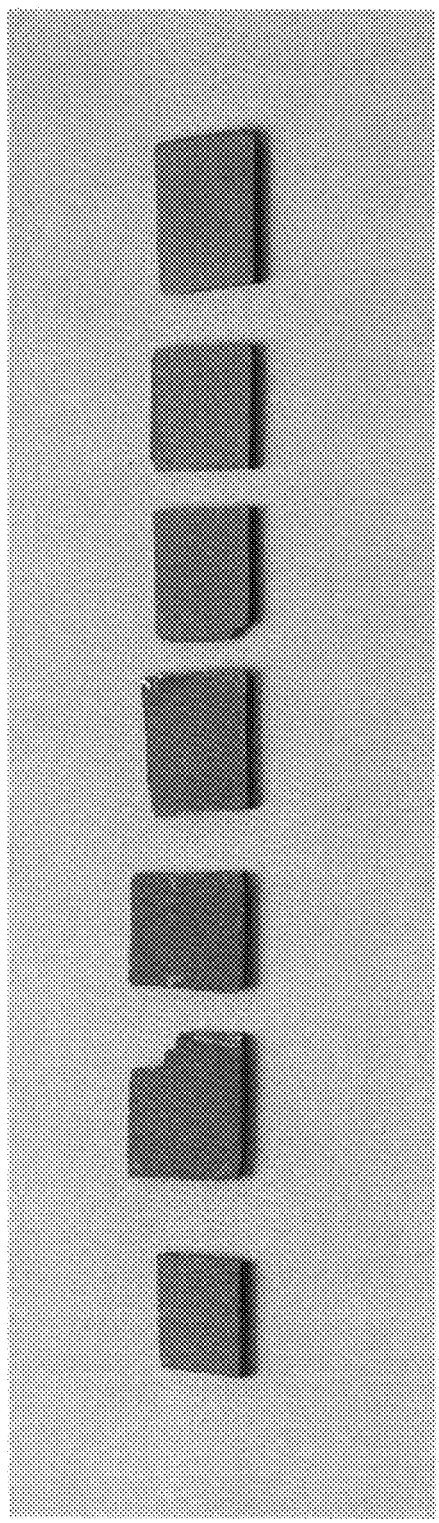
FIG. 4 is a photograph of SERS substrates fabricated on silicon with overgrowth times ranging from 0 (far left) to 15 minutes (far right), under white light illumination. The change in the perceived color indicates a variation in the frequency of the surface plasmon resonances.

Since the overgrowth reaction rate slows significantly at the narrow gaps between the particles, growth of individual nanoparticles is favored over coalescence of adjacent nanoparticles. This is advantageous in making the processes highly controllable (by varying the soaking time) and the product uniform. As shown in FIG. 3, the uniformity of the substrate is manifested in the marked peaks observed in the UV-vis attenuation spectra of SERS substrates fabricated on glass. The spectra contain two absorption peaks. The high photon energy peak is a resonance peak from the localized surface plasmons of the individual nanospheres. The low photon energy peak is from an extended surface plasmon delocalized over the array. These spectral features gradually evolve with overgrowth reaction time. As the particles in the nanosphere array grow larger and the gaps between them narrow, the localized surface plasmon resonance peak at 520 nm gradually red-shifts and the nascent lower-energy peak markedly increases in intensity and red-shifts. These spectral changes are a consequence of the increase in the coupling between plasmons on adjacent nanoparticles. As shown in FIG. 3, the spectral shifts due to varying the overgrowth times are also pronounced in reflection mode. Thus, the substrates can be tuned to accommodate for Raman spectrometers operating at a range of wavelengths from 500 to 900 nm.

Figure 5:
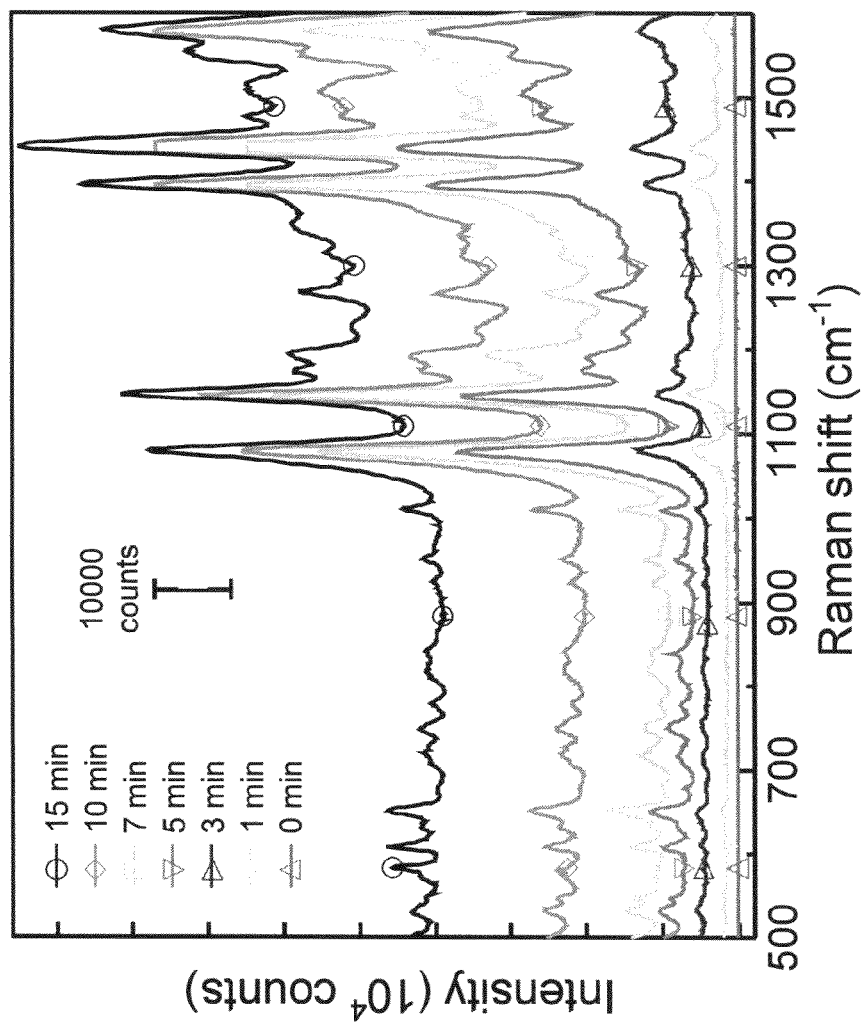
FIG. 5 is a surface-enhanced Raman spectra of 4-aminobenzenethiol on SERS substrates with overgrowth times ranging from 0 to 15 minutes. The spectra were shifted vertically for clarity.
Figure 6:
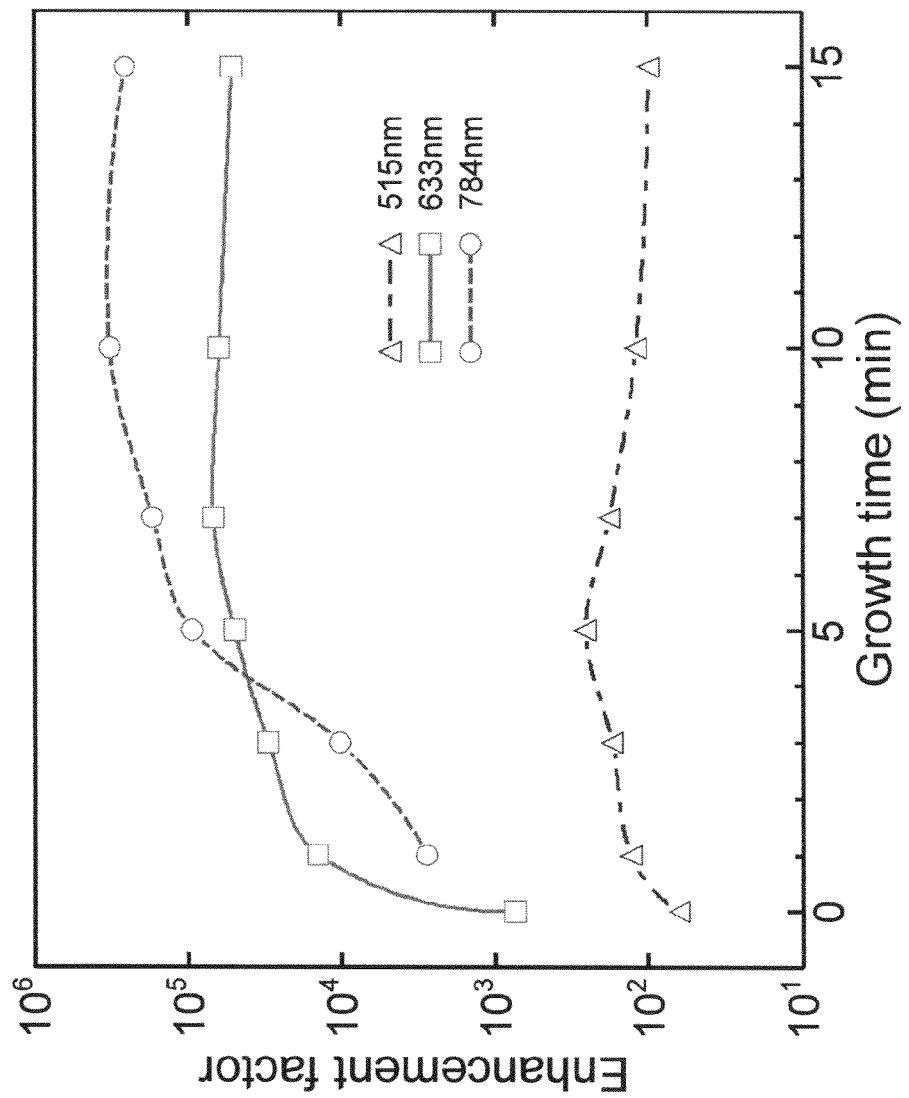
FIG. 6 is a graph depicting SERS substrate enhancement factor as a function of overgrowth time and probing (incident) laser wavelength.

SERS spectra were collected using a series of SERS substrates with varying thicknesses of overgrown gold over 15 nm gold nanosphere cores. Prior to the measurement, the substrates were soaked in a dilute solution of 4-aminobenzenethiol, rinsed with ethanol, and dried. The same SERS substrates were studied with 3 different lasers commonly found in Raman spectrometers. All the SERS spectra correspond to that of 4-aminobenzenethiol, however, the SERS signal intensity per molecule varies dramatically from SERS substrate to substrate. For example, as shown in FIG. 5, in the series of SERS spectra obtained with a He—Ne laser (633 nm) the maximum SERS enhancement is obtained with the substrate that was immersed for 7 minutes in the Au growth solution. The enhancement factors of the SERS substrates were calculated taking into account the surface area of the plasmonic nanospheres and the focal beam diameter. As shown in FIG. 6, the SERS substrate enhancement factor is dependent on the overgrowth time and the laser wavelength. To understand the trends in the magnitude of the enhancement factor we consider two guiding principles: i) The enhancement factor increases with the absolute value of the ratio of the real to imaginary components of the permittivity of the metal, $|\epsilon'/\epsilon''|$ (Kriebig, U., et al., Optical Properties of Metal Clusters, Springer, Berlin 1995; Mayergoyz, I. D., et al., Phys. Rev. Lett. 98:147401 (2007)). For gold, this ratio increases with the increase in wavelength in the range 500-900 nm (from ~1 to 33) (Palik, E., et al., Handbook of Optical Constants of Solids, Academic Press, Boston 1998). As a result, the highest enhancement factors were obtained using a 785 nm laser and the lowest using a 515 nm laser. ii) The optimal SERS performance is anticipated for substrates with surface plasmon resonance peaks slightly red-shifted with respect to the incident laser wavelength (Haynes, C. L., et al., J. Phys. Chem. B 107:7426 (2003)). For a given laser, there is an optimal overgrowth time (i.e., diameter to gap ratio) that maximizes the enhancement factor (Genov, D. A., et al., Nano Lett. 4:153 (2003)). The longer the wavelength of the laser, the longer the optimal overgrowth time. The optimal overgrowth time correlates with the shift in wavelength of the low-frequency (extended) surface plasmon resonance peak ($\lambda_{max}$=678 nm at 7 minutes and $\lambda_{max}$=768 nm at 10 minutes). In the case of the 515 nm argon ion laser, the high-frequency surface plasmon resonance peak matches the laser in all of the substrates. As a result, the variations in the structure of the substrate do not achieve any substantial increase in the SERS signal when the 515 nm laser is used. These experimental results are in good agreement with theoretical calculations of field enhancement in periodic 2D arrays (Genov, D. A., et al., Nano Lett. 4:153 (2003)).

TABLE 2

| Evolution of the enhancement factor as a function of overgrowth time. | |
| --- | --- |
| Reaction time (min) | Enhancement factor (average ± standard dev)[a] |
| 0 | 720 ± 640 |
| 1 | 3300 ± 1200 |
| 3 | 25300 ± 4900 |
| 5 | 89800 ± 6200 |
| 7 | 91100 ± 10000 |
| 10 | 54100 ± 5200 |
| 15 | 57900 ± 7600 |

[a]Analysis based on measurements on 120 different sites on each substrate using a 633 nm laser and a 1078 cm$^{-1}$ Raman peak of 4-ABT.

Figure 7:
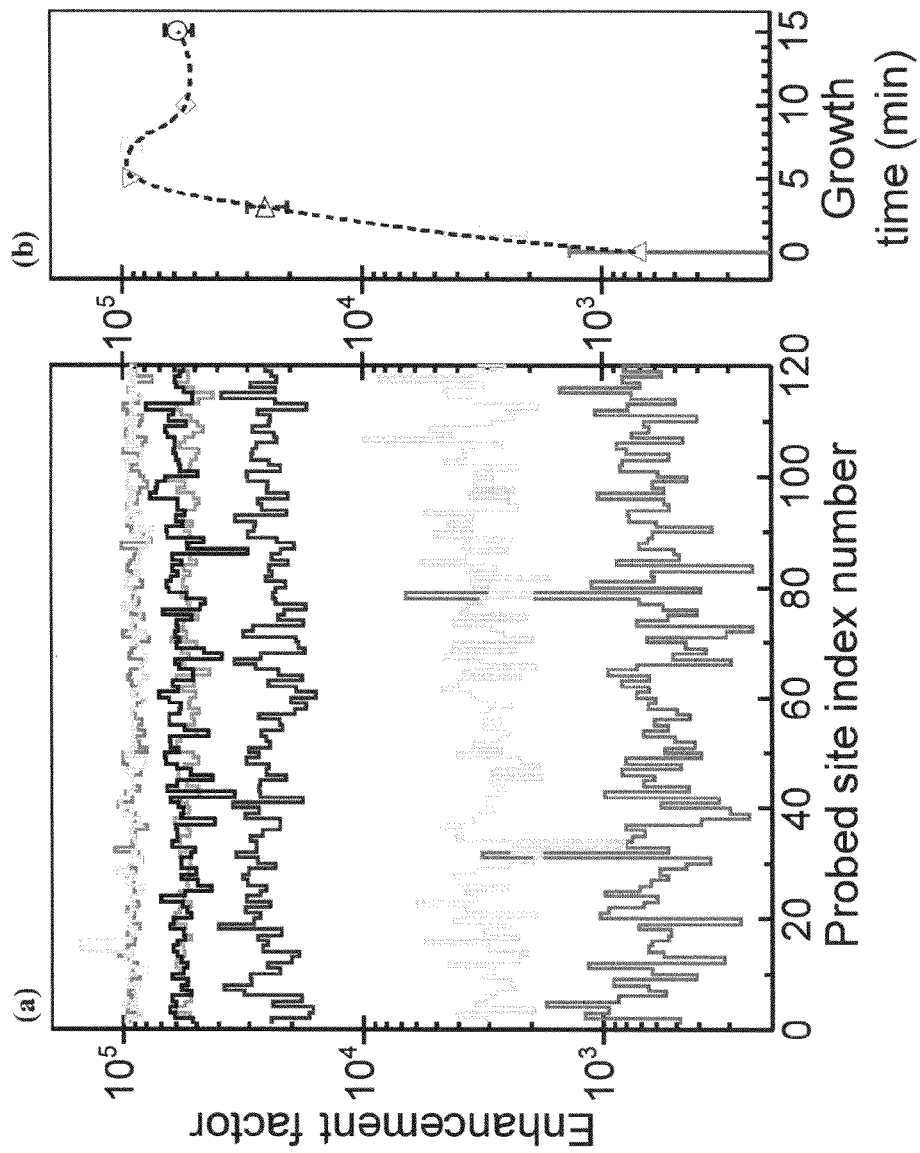
FIG. 7 is a graph describing SERS substrate enhancement factor as a function of overgrowth time with (a) showing a collection of data from 120 sites probed by a 633 nm laser and (b) providing average values and standard deviations.

The SERS substrates were fabricated on glass and silicon wafers with areas of at least 1 cm$^2$. The fabrication process is based on self-assembly and templating; errors in the registry of the polymer domains and in the position of the nanospheres are shown in FIG. 2. These structural defects may inadvertently produce variations in the SERS enhancement, location-by-location, reducing the utility of these SERS substrates. To mitigate this concern, each substrate was probed on 120 different sites and the SERS enhancement factor distribution was analyzed. As shown in FIG. 7 and Table 2, the site-to-site variations within a substrate are small, while the enhancement factor variations resulting from varying the overgrowth reaction time are significant. The results are most uniform for substrates with high enhancement factors (overgrowth time of 5-15 min). The standard deviation in the SERS substrate enhancement is only 10% of the average value. The data demonstrate that the SERS substrates are effectively homogeneous and that tuning the nanoparticle size and the gap size are effective ways to optimize the SERS enhancement factor. The substrates retained their SERS activity for at least 6 months of storage in air.

Example 2

PS-b-P4VP (number average molecular weight of polystyrene=47 kgmol$^{-1}$, number average molecular weight of poly (4-vinylpyridine)=10 kgmol$^{-1}$, polydispersity index=1.1), was purchased from Polymer Source, Inc. (Montreal, Canada), and used without further purification. PS-b-P4VP was dissolved in THF to yield a 0.5 wt % polymer solution. The polymer solution was filtered through a Millipore 0.45 µm poly(tetrafluoroethylene) filter. The molecular size of PS-b-P4VP in the polymer solution was measured using dynamic light scattering (DLS). The DLS procedure was performed at a 90° scattering angle and a 632.8 nm wavelength using a Zetasizer Nano ZS90 (Malvern Instruments Ltd., Malvern, United Kingdom). PS-b-P4VP films were prepared by spin-coating at 3000 rpm for 30 seconds on silicon substrates at different levels of relative humidity (RH). The RH during spin-coating was controlled by adding desiccant to a glass chamber enclosing the spinning chuck on which the substrate was placed. The RH was measured with a hydrometer inside the glass chamber. An alternate solvent of propylene glycol methyl ether acetate (PGMEA) was used in some experiments to scale the process up for larger substrate sizes in a clean room. For PGMAE, a 0.75 wt % solution concentration was used and this was spin-coated at 2000 rpm for 30 seconds. As-spun films at 23% RH were annealed in THF vapor, deionized water vapor, or THF/deionized water vapor at room temperature for 6 hours. Thin film surface morphology was characterized using a Dimension 3000 atomic force microscope (AFM) from Digital Instruments, Inc. (Tonawanda, N.Y.). Silicon tips with spring constants ranging between 20.0 and 80.0 N m−1 were used. To measure the thin film thickness, the polymer films deposited on silicon substrates were scratched with a scalpel, and AFM images were taken across the borders of the scratches far enough away to ensure correct film thickness measurement. The contact angle of water on a PS-b-P4VP film annealed in THF vapor was measured using a Ramé-Hart Model 250-00 goniometer.

1,4-dibromobutane (DBB) was purchased from Sigma Aldrich (St. Louis, Mo.) and used without further purification. P4VP blocks in a PS-b-P4VP film were quaternized in DBB vapor. The degree of quaternization was measured using XPS on a Kratos AXIS 165 x-ray photoelectron spectrometer using a monochromatic Al Kα x-ray source (1486.6 eV). The instrument was operated in hybrid mode, with survey and high resolution spectra collected at pass energies of 160 eV and 20 eV, respectively. The anode voltage was 12 kV and the anode current was 20 mA. The pressure in the analysis chamber was maintained at $6.7 \times 10^{-6}$ Pa or lower during each measurement. The samples were mounted on standard sample studs by means of double-sided adhesive tape. The core-level signals were obtained at a photoelectron take-off angle of 90° (with respect to the sample surface). Citrate-capped gold colloid with 15 nm mean particle diameter was purchased from BBInternational (Cardiff, United Kingdom). The positively charged PS-b-P4VP film was immersed in a negatively charged gold nanoparticle suspension in water, thoroughly washed in deionized water and then blow-dried in air. Scanning electron microscopy (SEM) observation was conducted using a Hitachi SU-70 Schottky field emission gun SEM working at 3 kV or 10 kV accelerating voltage and a working distance of approximately 5.5 mm.

PS-b-P4VP with 0.175 P4VP weight fraction, which is expected to form hexagonally ordered P4VP cylinders in bulk (Peinemann, K. V., et al., *Nature Mater.* 6:992 (2007)), was dissolved in THF. As THF has a preferential affinity for PS compared to P4VP (reported Flory-Huggins interaction parameters $\chi$PS-THF=0.35 and $\chi$P4VP-THF=0.6) (Park, S., et al., *Macromolecules* 27:3276 (2007)), PS-b-P4VP micelles of a PS corona and a P4VP core have been observed in THF solutions (Antonietti, M., et al., *Macromolecules* 40:9059 (1994)). However, the micellization is highly dependent on a number of variables, such as P4VP block ratio, P4VP block molecular weight and PS-b-P4VP concentration (N. Ali and S. Y. Park, *Langmuir* 24:9279 (2008)). The PS-b-P4VP solution in THF was optically clear, and the hydrodynamic radius ($R_h$), obtained from the DLS measurement, is 7.5 nm, indicating that no large aggregates are formed, probably due to the low P4VP weight fraction (~0.175), the small number average molecular weight of PS-b-P4VP, and the low polymer concentration. It was previously reported that for a PS-b-P4VP block copolymer (number average molecular weight of polystyrene=47.6 kgmol$^{-1}$, number average molecular weight of poly(4-vinylpyridine)=20.6 kgmol$^{-1}$, polydispersity index=1.14, approximately twice the P4VP block molecular weight as compared to the polymer), the $R_h$ in a 0.5 wt % PS-b-P4VP/THF solution was 6 nm (Peinemann, K. V., et al., *Nature Mater.* 6:992 (2007)). The effect of the preferential affinity of THF for PS was observed in the morphologies of as-spun and THF annealed PS-b-P4VP films.

Figure 9:
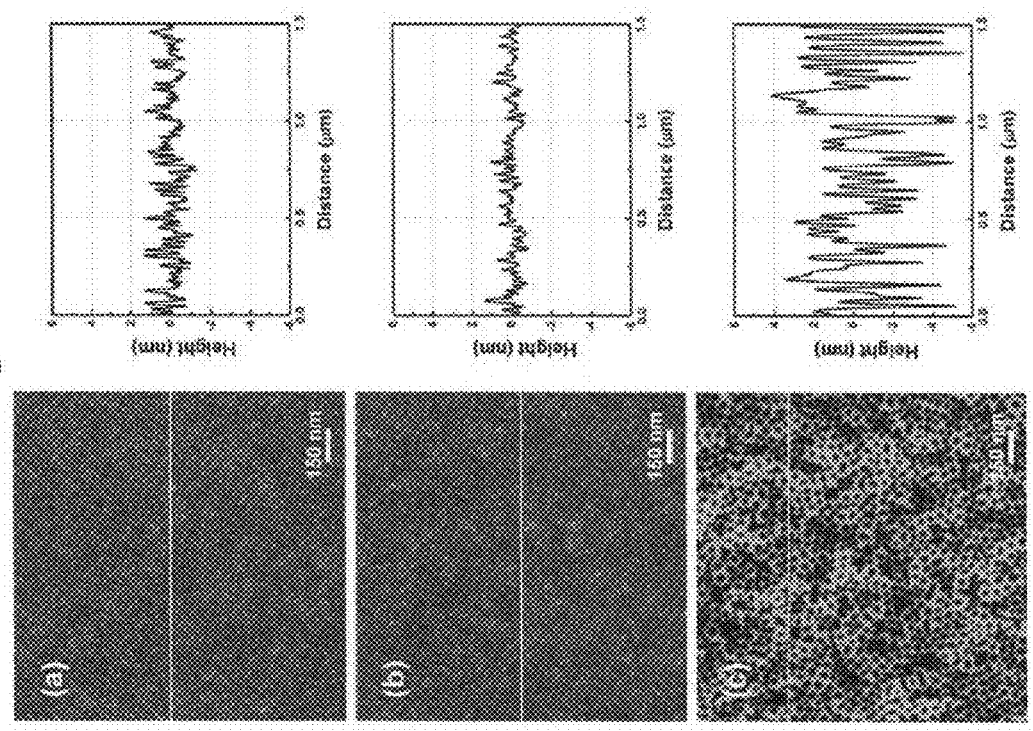
FIG. 9 is a series of AFM images of the as-spun PS-b-P4VP films as a function of relative humidity (RH) during spin-coating at (a) 23%; (b) 37%; and (c) 50%. All images were set to the same height scale (15 nm).

FIG. 9 shows AFM height images of as-spun films depending on the RH during spin-coating. As shown in FIGS. 9a and 9b, at relatively dry conditions, protruding convex nodules in a continuous matrix are observed with the nodules being less elevated at 37% RH. The observed morphologies are formed due to the differing evaporation rates of the THF in the different domains, as has been observed in as-spun films from homopolymer mixture solutions, where the solvent has a preferential affinity for one of the homopolymers (Walheim S., et al., *Science* 283:520 (1999); Boltau M., et al., *Nature* 391:877 (1998); Tanaka K., et al., *Macromolecules* 29:3232 (1996); Walheim S., et al., *Macromolecules* 30:4995 (1997); Cui L., et al., *Polymer* 46:5334 (2005). During spin-coating of the PS-b-P4VP solutions, the THF evaporates and phase separation occurs due to the strong repulsive interaction between the blocks. Since THF prefers PS to P4VP, the P4VP domains are quickly depleted of solvent and solidify first. Subsequent evaporation of the remaining solvent leads to collapse of the PS matrix, resulting in elevated P4VP nodules. The solvent evaporation from the surface during spin-coating leads to a reduction of surface temperature, causing condensation of water on the surface under humid conditions. As water is completely miscible with THF, this can alter the THF evaporation rate and affect the morphology of the as-spun film at high RH conditions. As shown in FIG. 9c, the film spin-coated at 50% RH forms pits instead of elevated nodules for the P4VP domains. The center-to-center distance increased from 25 nm under dry conditions to 40 nm under humid conditions. The condensed water would be distributed within the hydrophilic P4VP domains, and make P4VP chains swell. The P4VP domains solidify last after the complete evaporation of the THF and condensed water, leading to an elevated PS matrix. A similar effect of humidity during spin-coating on the morphologies of as-spun PS/poly(2-vinylpyridine) (P2VP) blend films (Cui, L., et al., *Polymer* 46:5334 (2005)) and PS-b-P2VP micelle films (Krishnamoorthy, S., et al., *Adv. Funct. Mater.* 16:1469 (2006)) has been observed.

As high RH is often undesirable for manufacturing, the as-spun film fabricated at relatively low RH (23%) was chosen and annealed in THF vapor for 6 hours at room temperature to induce a high degree of lateral ordering. The film annealed in THF vapor shows a long-range hexagonally ordered structure with a center-to-center distance of 41.5 nm, indicating reorganization of the PS-b-P4VP film structure through THF annealing. The high degree of lateral ordering is beneficial for nanotemplating applications. The annealed PS-b-P4VP film may have either a micellar structure with only PS exposed to the air surface or a structure of hexagonally arranged P4VP cylinders in a PS matrix with both blocks exposed to the air surface.

Figure 10:
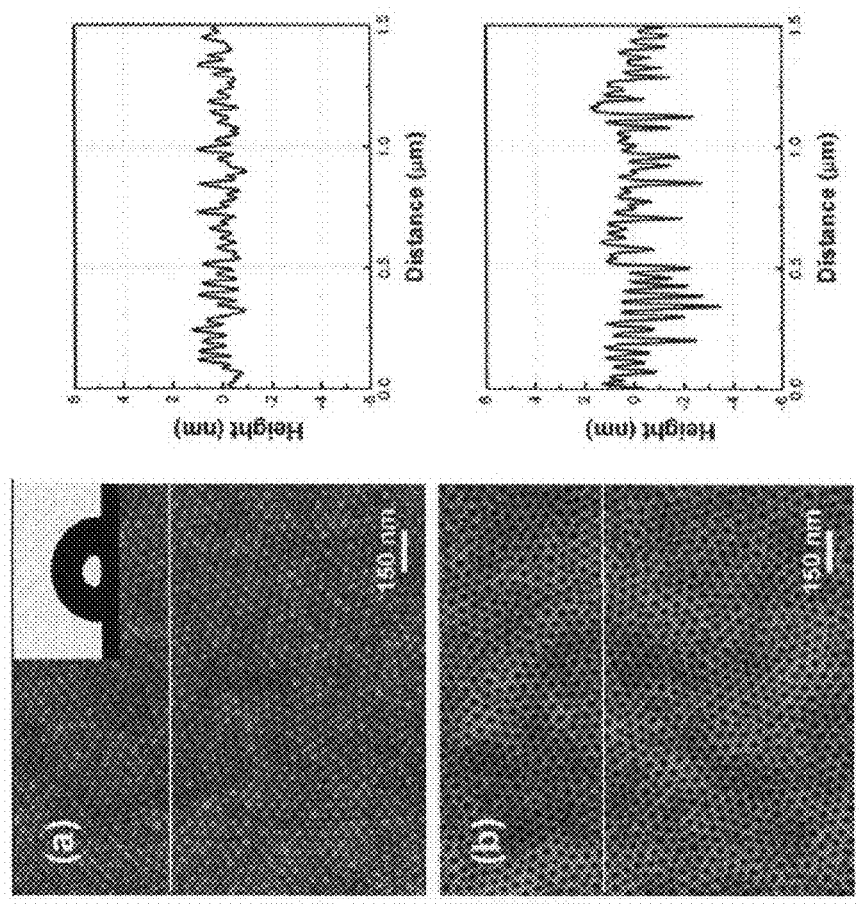
FIG. 10 is a series of AFM height images of PS-b-P4VP films annealed in (a) THF; and (b) THF/deionized water (50/50 v/v). All images were set to the same height scale (15 nm). The inset in (a) shows a photograph of a water droplet on the THF annealed film.

A critical difference between a PS-b-P4VP spherical micelle film and a PS-b-P4VP vertically oriented cylinder film relates to whether the P4VP domains are exposed to the air surface. In a PS-b-P4VP micelle film with a PS corona, the surface of the film should be only PS with no P4VP exposed. In order to verify the film structure in FIG. 10a, the contact angle was measured for water on the THF annealed film, and a typical result is shown in FIG. 10a as an inset To increase the accuracy of the measurements, six different positions were measured. The contact angle for water on the annealed PS-b-P4VP film was on average 83.3°, which is less than the contact angle (90°) for water on a PS film and larger than the contact angle (75.6°) for water on P4VP film (Yan, C., et al., *ACS Nano* 6:2096 (2012)). The contact angle for water on an as-spun PS-b-P4VP spherical micelle film was reported to be 105°, higher than observed for a pure PS film (Hwang, W., et al., *Nanotechnology* 16:2897 (2005)). The result indicates that hydrophilic P4VP domains in the THF annealed PS-b-P4VP films are exposed to the air surface and the film structure is vertically oriented P4VP cylinders.

The film thicknesses of the as-spun film and the annealed film were 25 nm and 24 nm, respectively. The as-spun film was gray in color. During annealing in THF vapor, the color of the film changed and eventually remained yellow, indicating that the film thickness increased due to swelling with THF. When the film was removed from the THF vapor, the film color quickly turned gray as the THF evaporated. This process is very similar to what happens during spin-coating from THF solution. The resulting P4VP domains in the THF annealed films are also elevated, as is observed in the as-spun films. When PS-b-P4VP films are annealed in THF vapor, it is likely that self-assembly occurs at the air surface and ordering then propagates through the film, resulting in elevated P4VP domains. To verify this, the surface structure of the PS-b-P4VP film was inverted by annealing the as-spun PS-b-P4VP film fabricated at the low RH conditions (RH: 23%) in THF/water vapor. When it was exposed to vapor from a 50:50 v/v THF/water mixture, the as-spun film turned yellow as the PS-b-P4VP film swelled. When PS-b-P4VP films are swollen with THF, water vapor can dissolve into the films as water is completely miscible with THF and can hydrogen bond to the P4VP block. An AFM height image of the THF/water annealed film is shown in FIG. 10b. While the film annealed in THF/water vapor formed a hexagonally ordered PS-b-P4VP cylindrical structure, the P4VP domains became pits, in contrast to the THF annealed film case, indicating that dissolved water altered the THF evaporation rate in the P4VP domains. It is notable that the center-to-center distance between P4VP cylinders increased from 41.5 nm to 47 nm. Although it is unknown whether the center-to-center distance between P4VP domains at the surface of the PS-b-P4VP film annealed in THF/water vapor is maintained throughout the entire thickness, it is believed that dissolved water swelled P4VP domains as observed in FIG. 9c, giving rise to the change in the center-to-center distance. For comparison, the as-spun film was also annealed in water vapor. When the as-spun film was annealed in water vapor, its color did not change, indicating no change in the film thickness as water is a non-solvent for PS-b-P4VP. The surface morphology of the annealed film is identical to that of the as-spun film as shown in FIG. 9a. This suggests that the film morphology is a hexagonal structure of P4VP cylinders in a PS matrix grown via directional solvent evaporation. As the hexagonally ordered P4VP domains generated by THF or THF/water annealing are exposed to the air surface, the domain structure can be used to control the positioning of nanoparticles on the basis of selectivity of surface interactions. As the THF annealed film showed better ordering and regularity in P4VP domain size, the THF annealed PS-b-P4VP film was selected for use as a template. P4VP domains in the THF annealed film were first quaternized to allow the generation of an ordered nanoparticle array via Coulombic interactions of the negatively charged gold nanoparticles with positively charged quaternized P4VP domains. P4VP quaternization (and crosslinking) was accomplished by exposing the film to dibromobutane (DBB) vapor (Lam, Y. M., et al., *J. Colloid Interface Sci.* 317:255 (2008)). After quaternization, the film was washed with hexane and dried in air. The film structure was maintained after quaternization, as confirmed using AFM.

To verify P4VP quaternization, the quaternized PS-b-P4VP film was characterized using XPS and the result was compared to an unquaternized PS-b-P4VP film, as shown in FIG. 8. To compensate for surface charging effects, all core-level spectra were referenced to the C 1s hydrocarbon peak at 284.8 eV. The N 1s core-level spectrum of the untreated PS-b-P4VP film (black dotted line) indicates a peak at 399.4 eV attributed to the nitrogen in the pyridine group. After quaternization, the N 1s core-level spectrum (gray dotted line) shows an additional XPS peak at a binding energy above 402 eV, attributable to the positively charged nitrogen (Hu, F. X., et al., *Biotechnol. Bioeng.* 89:474 (2005)).

The N 1s region was fit to two peaks with a 70%/30% Gaussian/Lorentzian product function of equal full width at half-maximum after application of a Shirley background. The degree of quaternization of the pyridine groups was calculated to be 66%.

Figure 11:
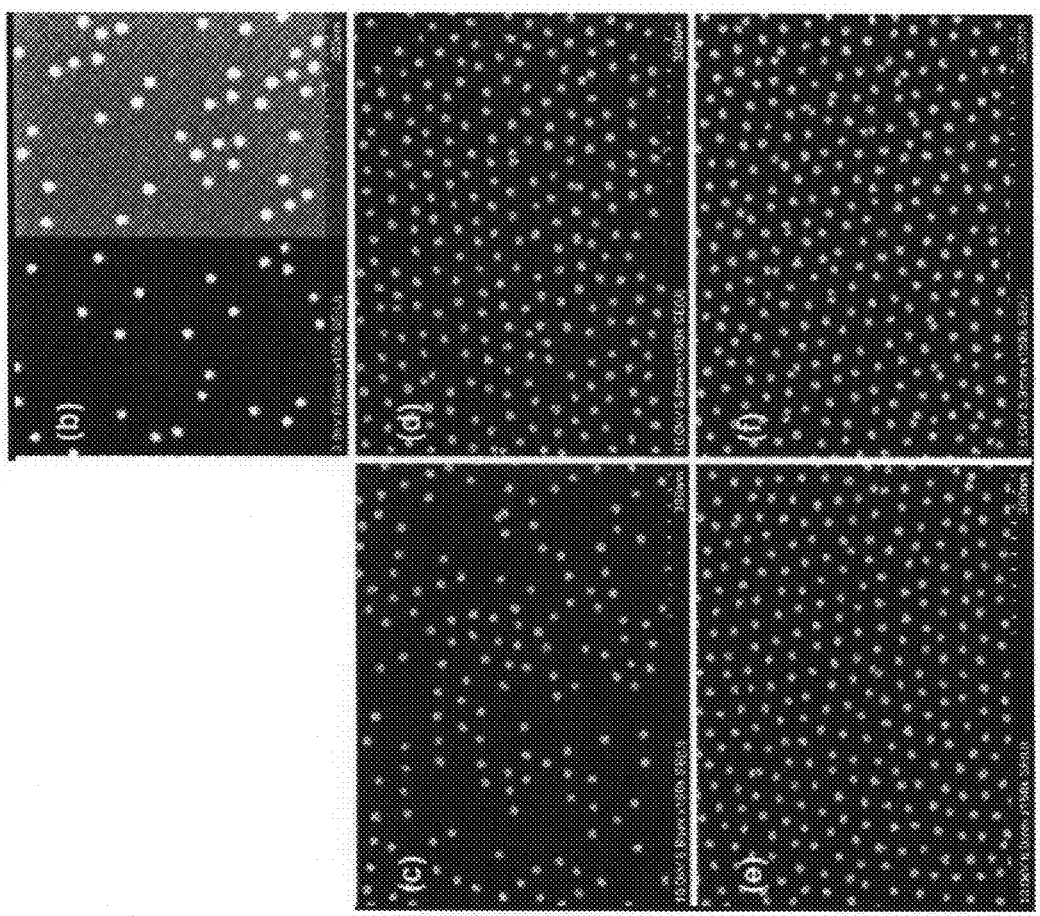
FIG. 11 is a series of SEM images of gold nanoparticles on the quaternized PS-b-P4VP film after the substrate was immersed in a nanoparticle solution for (b) 5 minutes; (c) 20 minutes; (d) 1 hour; (e) 3 hours; and (f) 6 hours.

The evolution of an ordered array of gold nanoparticles on the quaternized PS-b-P4VP thin film was followed using SEM as shown in FIGS. 11*b-f*. To show the underlying block copolymer pattern, the contrast and brightness of the right half of FIG. 11*b* were enhanced. P4VP domains appear slightly brighter compared to the PS matrix due to elevation. As shown in FIG. 11*b*, the hexagonally ordered block copolymer structure is maintained after the quaternization and self-assembly. The gold nanoparticles are located exclusively on the P4VP domains in the quaternized films, indicating that the self-assembly was driven by electrostatic interactions. Since the gold nanoparticles are not forced to sit on the center of each quaternized P4VP domain, the regularity of the center-to-center distance between gold nanoparticles is less than the underlying block copolymer pattern although they show the same average value.

Figure 12:
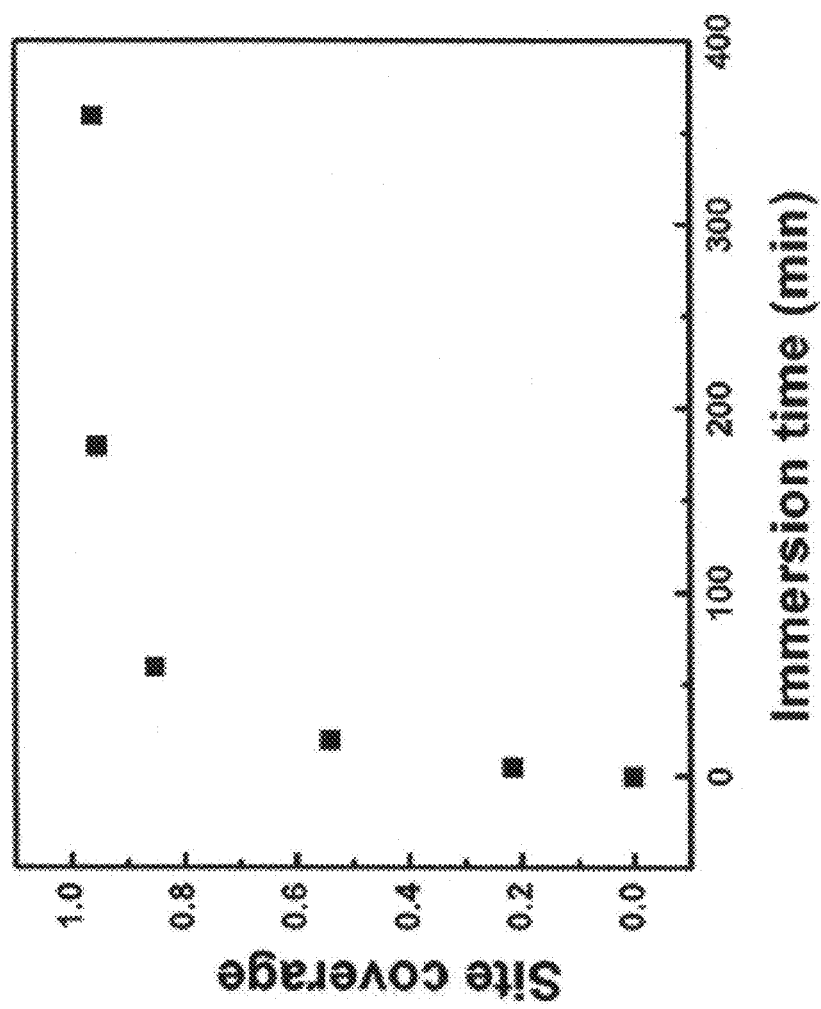
FIG. 12 is a graph depicting the site coverage of block copolymer thin films with gold nanoparticles as a function of immersion time in a nanoparticle suspension.

The nanoparticle/block copolymer site coverage was calculated from the SEM images as a function of immersion time. Here, the site coverage is defined by the average number of gold nanoparticles over the average number of P4VP domains. The average number of gold nanoparticles in a 0.5 $\mu m^2$ area was calculated from the SEM images using ImageJ software (Abramoff, M. D., et al., *Biophoton. Int* 11:36 (2004)). To increase accuracy, at least four different SEM images per immersion time were analyzed. When a nanoparticle pair was observed on a P4VP domain, it was counted as a single particle. The average number of P4VP domains per 0.5 $\mu m^2$ was counted from four different SEM images of the quaternized PS-b-P4VP films without per 0.5 $\mu m^2$ was 322. This value is close to 355, which is the number of P4VP domains per 0.5 $\mu m^2$ calculated from the measured center-to-center distance (41.5 nm) between P4VP domains assuming an ideal hexagonal structure. The results are summarized in FIG. 12. The site coverage rapidly increases at the early stage and then plateaus as the immersion time increased. Almost all P4VP domains (about 97%) were decorated with gold nanoparticles within 3 hours. Immersion for longer than 3 hours did not change the site coverage, but the fraction of nanoparticle pairs increased from 0.01 to 0.035. Some quaternized P4VP domains can accommodate more than one nanoparticle, depending on how far displaced from the center of the P4VP domain the first nanoparticle is immobilized. The ratio of pairs to unimers could potentially be controlled by varying the ratio of the domain to nanoparticle size.

To scale up the fabrication process to large area substrates, the process was performed in a cleanroom facility, and the polymer was dissolved in propylene glycol methyl ether acetate (PGMEA) instead of THF. PGMEA is a widely used clean room solvent with low health and environmental impacts. PGMEA is also a relatively slowly evaporating solvent, which enables solution dispensing over large wafers with uniform film thickness control through spin-coating. Using PGMEA the fabrication process has been extended to 4" wafers.

Figure 13:
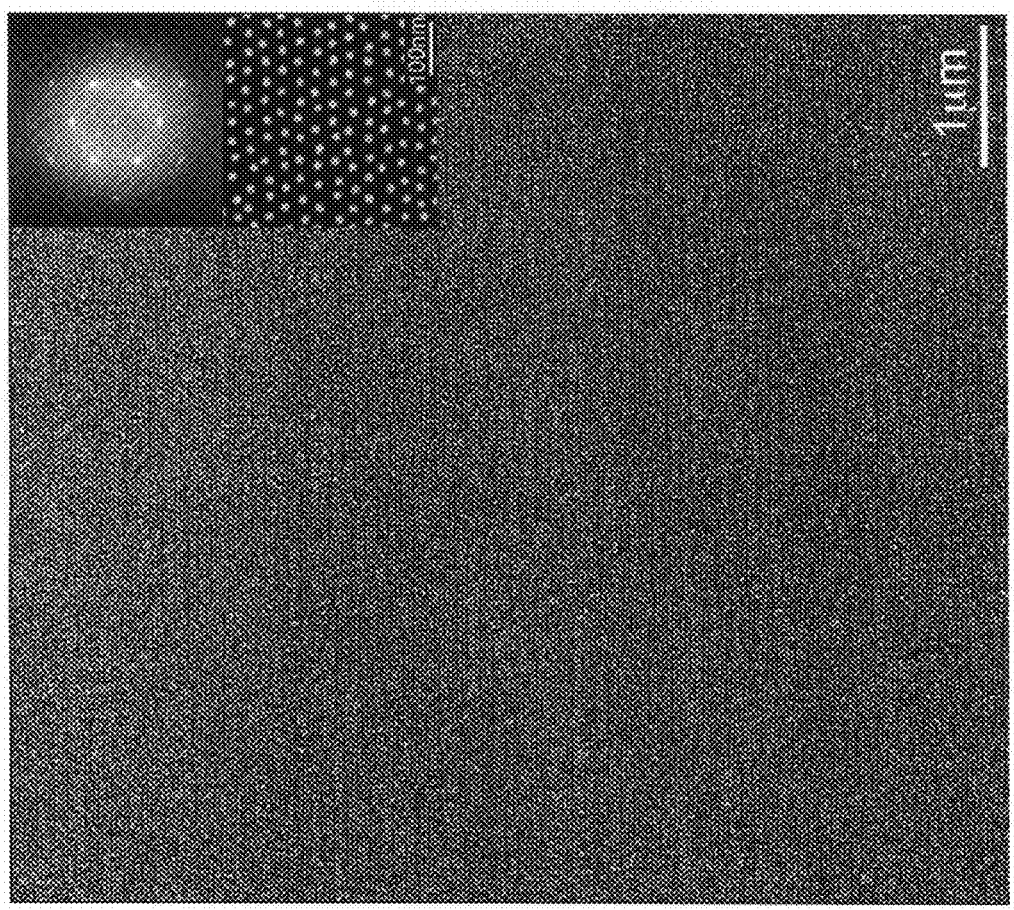
FIG. 13 is a series of SEM images taken from a four-inch wafer sample spin cast using polyglycol methyl ethyl acetate (PGMEA) showing a large gold nanoparticle array domain. The top inset is a fast Fourier transform (FFT) of an area of the wafer approximately 100 µm$^2$ in size and the lower inset shows a higher magnification SEM micrograph. The average domain size in the films is approximately 100 µm$^2$.
Figure 14:
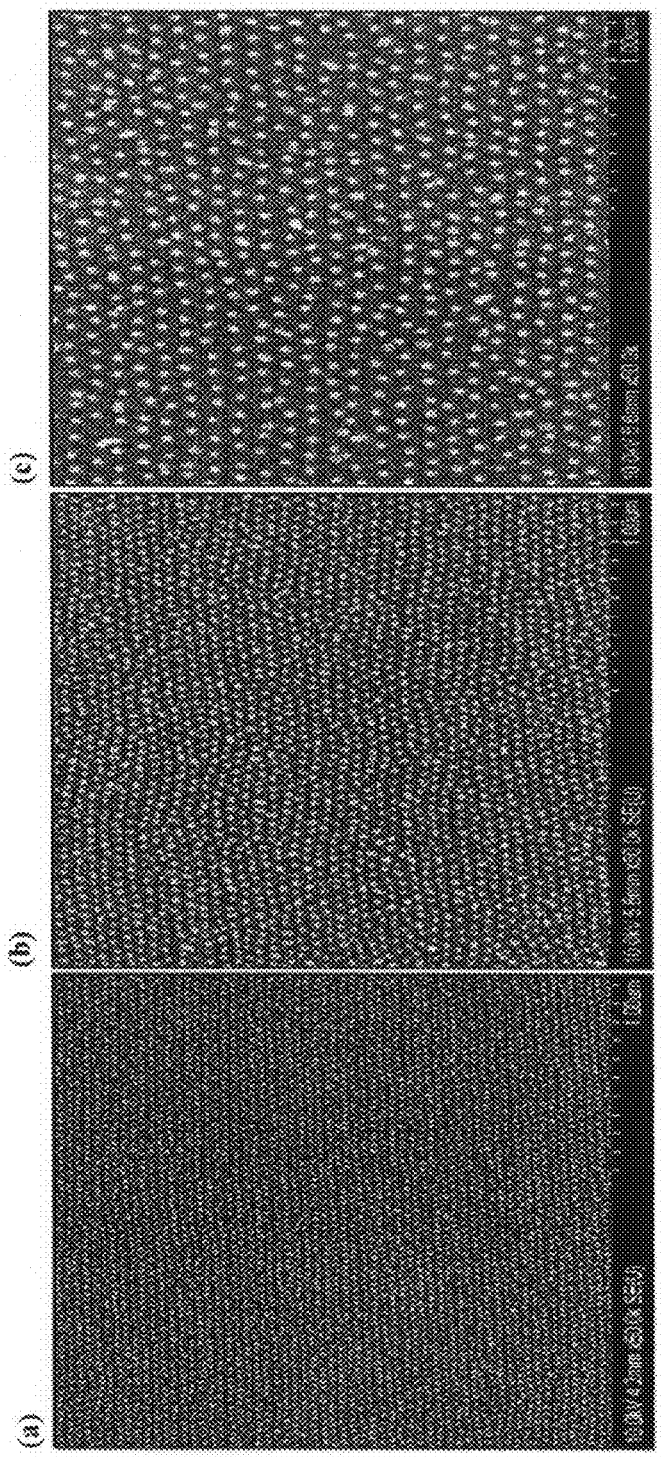
FIG. 14 is a series of three SEM images of gold nanoparticles of different sizes with block copolymers of different molecular weights of: (a) 15 nm diameter gold nanoparticles on a PS-b-P4VP block polymer (number average molecular weight of polystyrene of 47 kg/mol and of poly(vinyl-4-pyridine) of 10 kg/mol, intrinsic polymer period ($L_0$) of 31.5 nm); (b) 20 nm diameter gold nanoparticles on a PS-b-P4VP block polymer (number average molecular weight of polystyrene of 47.5 kg/mol and of poly(vinyl-4-pyridine) of 15.5 kg/mol, intrinsic polymer period ($L_0$) of 44 nm); and (c) 30 nm diameter gold nanoparticles on a PS-b-P4VP block polymer (number average molecular weight of polystyrene of 175 kg/mol and of poly(vinyl-4-pyridine) of 65 kg/mol, intrinsic polymer period ($L_0$) of 88 nm).
Figure 15:
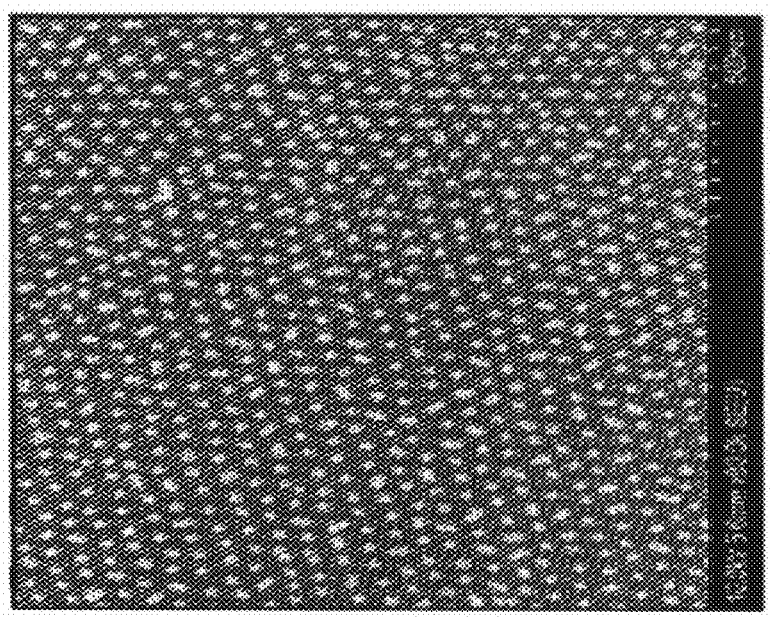
FIG. 15 is a SEM image of 20 nm diameter gold nanoparticles on a PS-b-P4VP block polymer (number average molecular weight of polystyrene of 75 kg/mol and of polyvinyl-4-pyridine) of 25 kg/mol, intrinsic polymer period ($L_o$) of 54 nm).
Figure 16:
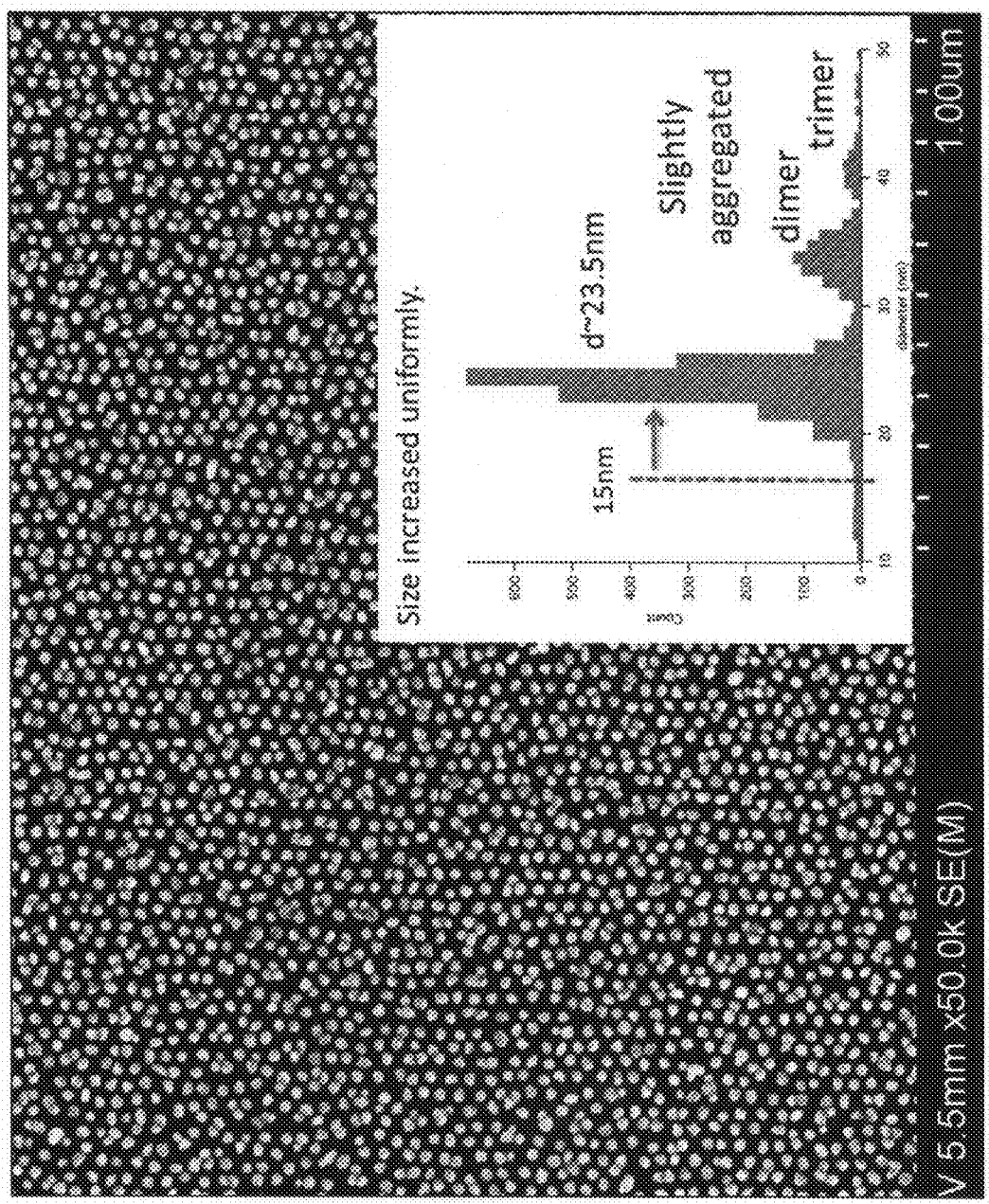
FIG. 16 is a SEM image of silver overgrowth on 15 nm diameter gold seeds for 5 minutes. The inset is a bar graph that shows that the size increased uniformly with the nanoparticle diameter increasing from 15 nm to 23.5 nm.
Figure 17:
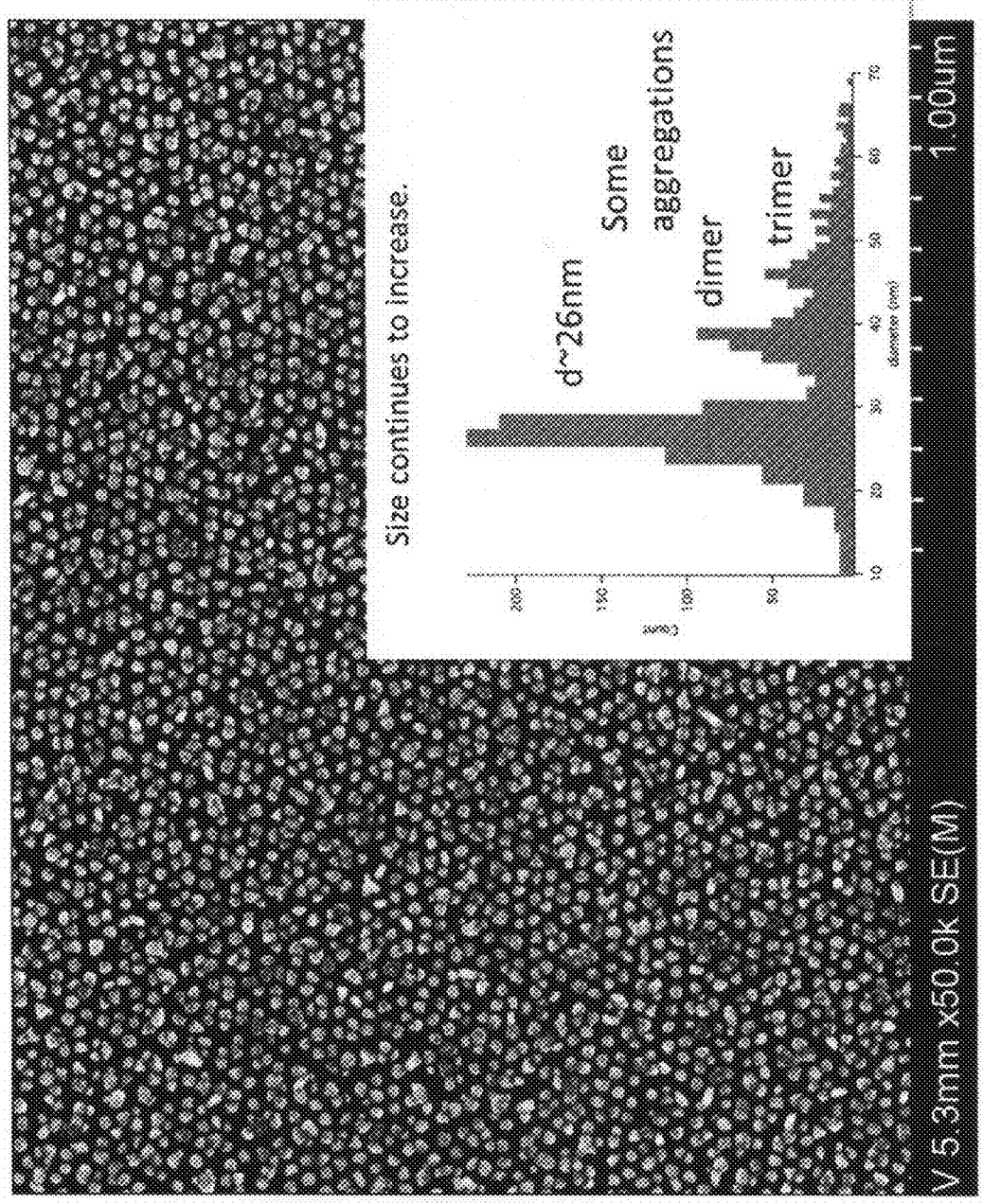
FIG. 17 is a SEM image of silver overgrowth on 15 nm diameter gold seeds for 10 minutes. The inset is a bar graph that shows that the size increased uniformly with the nanoparticle diameter increasing from 15 nm to 26 nm.
Figure 18A:
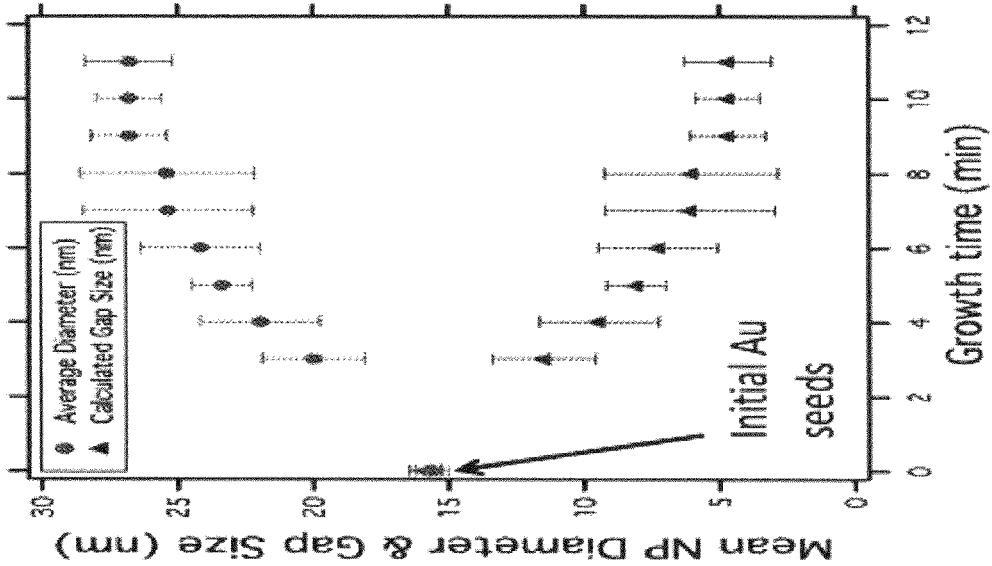
FIGS. 18A and 18B are graphs depicting: (A) the area of coverage of gold nanoparticles measured using ImageJ software based on SEM micrographs; and (B) the average diameter and calculated gap size based on the area of the isolated nanoparticles.
Figure 18B:
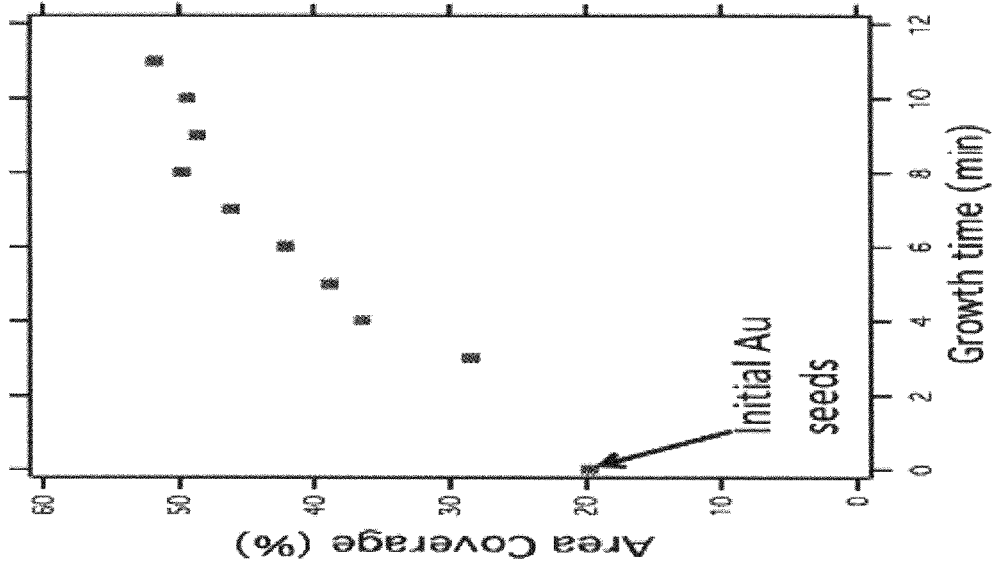
Figure 19A:
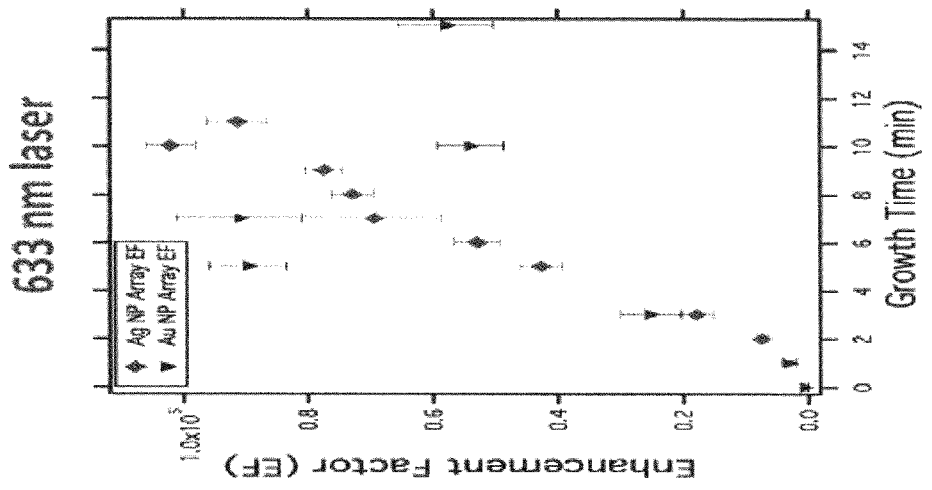
FIGS. 19A and 19B are graphs depicting: (A) the enhancement factor of the silver and gold nanoparticle array under green laser (532 nm); and (B) the enhancement factor of the silver and gold nanoparticle array under red laser (633 nm).
Figure 19B:
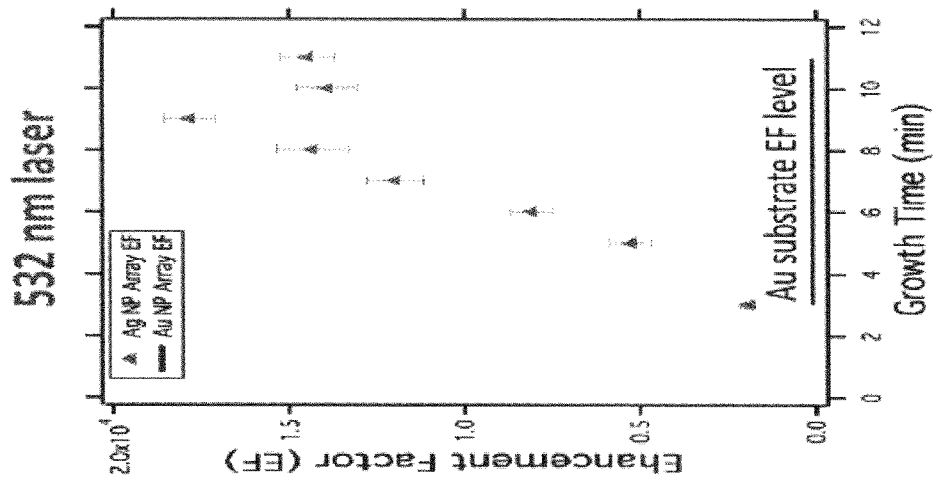
Figure 20:
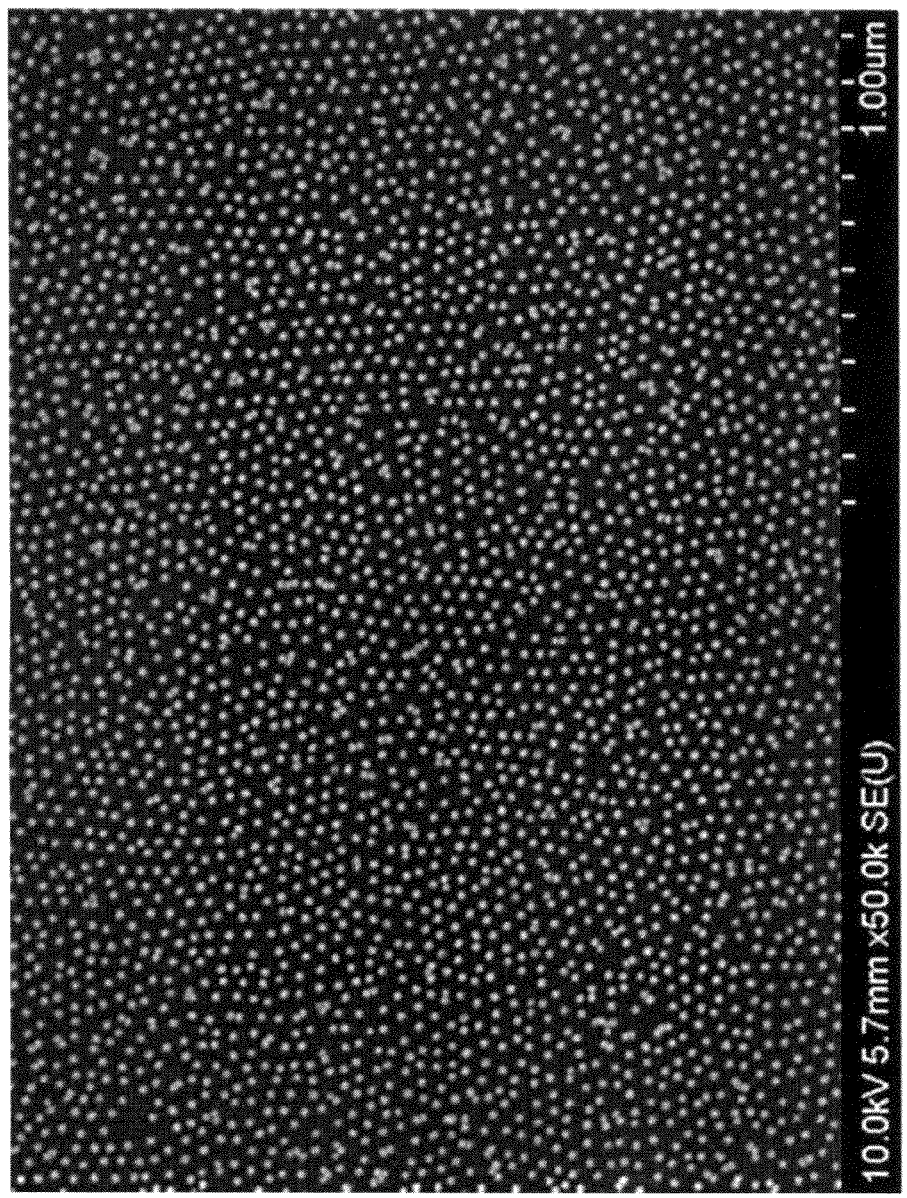
FIG. 20 is an SEM image of a nanoparticle array of 20 nm CdSe/ZnS core-shell quantum dots on a PS-b-P4VP block copolymer film.
Figure 21:
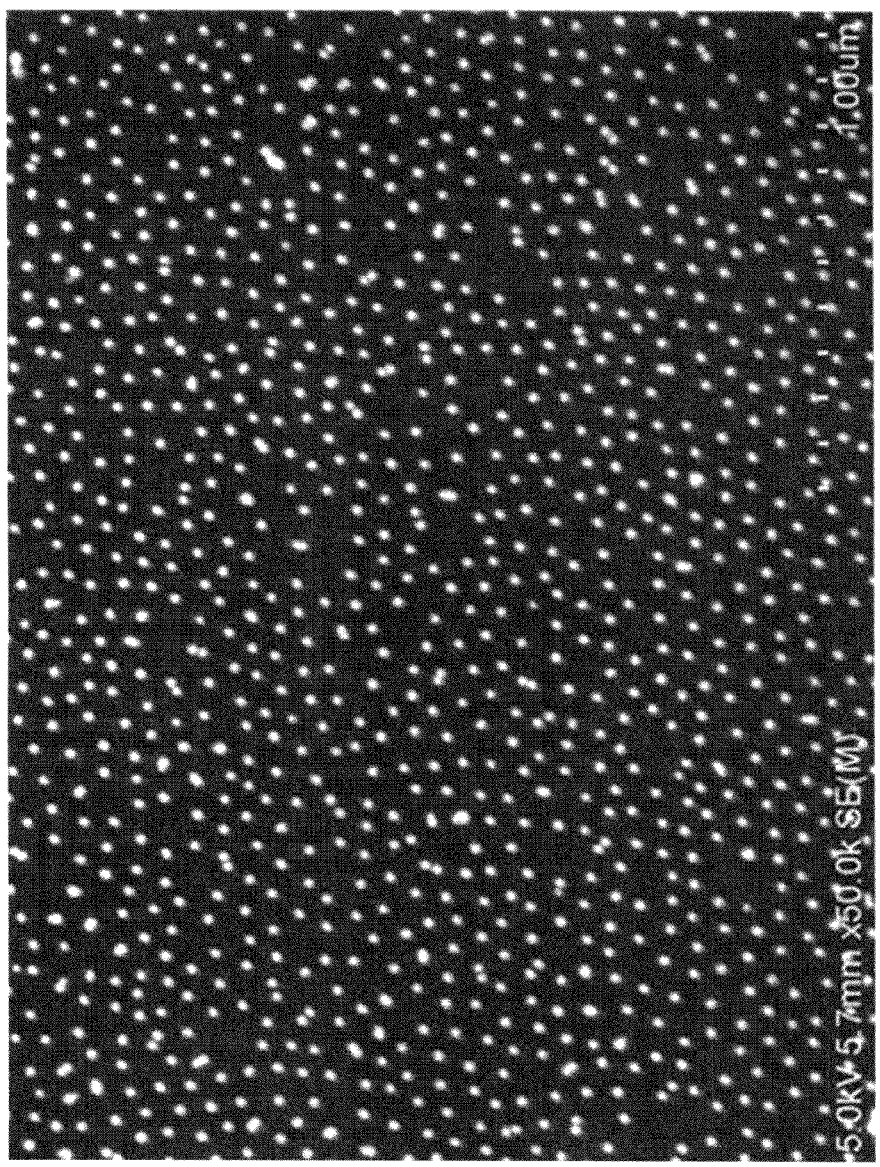
FIG. 21 is an SEM image of a nanoparticle array of 20 nm Ag nanoparticles on a PS-b-P4VP ($M_w$=93,000:35,000) block copolymer film.
Figure 22:
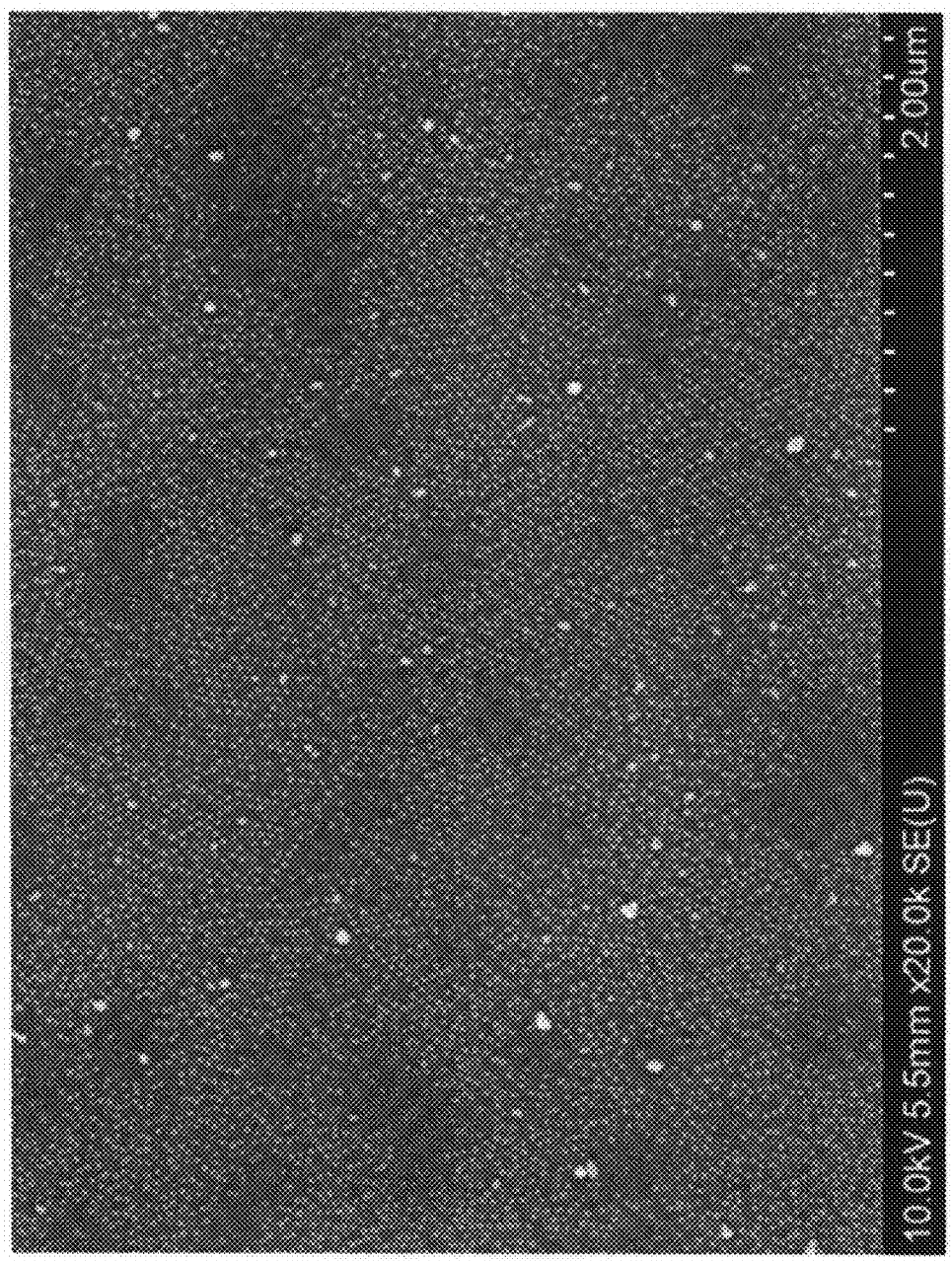
FIG. 22 is an SEM image of a nanoparticle array of 20 nm Ag nanoparticles on a PS-b-P4VP ($M_w$=75,000:25,000) block copolymer film.
Figure 23:
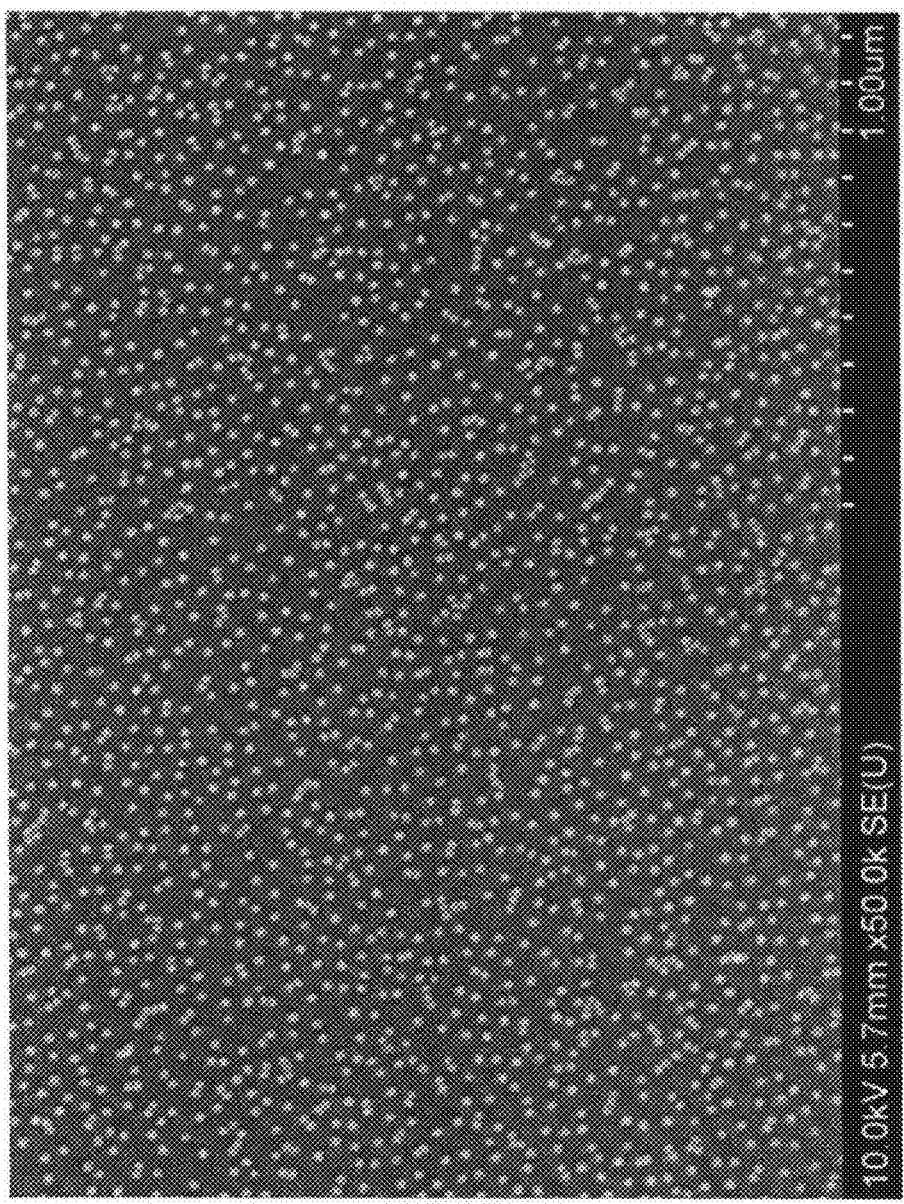
FIG. 23 is an SEM image of a nanoparticle array of 15 nm magnetic iron oxide nanoparticles on a PS-b-P4VP ($M_w$=124,000:12,000) block copolymer film.

The process resulted in a uniform hexagonal array of gold nanoparticles on the entire wafer. FIG. 13 shows an SEM micrograph of part of a hexagonally ordered gold nanoparticle array approximately 100 $\mu m^2$. The top inset fast Fourier transform (FFT) is from the entire 100 $\mu m^2$ domain in the original SEM micrograph, indicating that the ordering extends over relatively large areas. Off the edge of the image in FIG. 13 are other domains with different orientations. Over the area of a single domain the hexagonal orientation is uniform, as demonstrated by the single-crystal-like FFT pattern inset in FIG. 13. Although the orientation is uniform within a domain there are defects within the pattern. The average major defect density was found to be about 4 defects/$\mu m^2$, where major defects are defined as nanoparticle pairs, large nanoparticles, or site vacancies. Nanoparticles that were slightly deviating from their ideal position were not considered major defects.

The number of defects is also affected by the quality of gold colloid solution which can contain large nanoparticles and aggregated nanoparticle pairs. As noted, the gold colloid solution was purchased from BBinternational (Cardiff, United Kingdom) and while it has a relatively uniform size distribution (the polydispersity is less than 5% as measured using small angle x-ray scattering), there can be some aggregation with aging or variability between batches.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A method of producing a nanoparticle array comprising:
   (a) applying a block copolymer onto a substrate to give a thin film;
   (b) reacting the applied block copolymer of (a) with a functionalizing agent; and
   (c) immersing the thin film of (b) in a nanoparticle suspension to give a nanoparticle array;
   wherein the nanoparticles are dispersed on the block copolymer.

2. The method of claim 1, further comprising:
   (d) immersing the nanoparticle array of (c) in a growth solution.

3. The method of claim 2, wherein the growth solution comprises a metal atom selected from the group consisting of Ag, Au, Cu, and Li or a non-metal selected from the group consisting of $SiO_2$, $TiO_2$, $Fe_2O_3$, $Al_2O_3$, Cds, CdSe, PbS, PbSe, and $Bi_2S_3$.

4. The method of claim 1, wherein the block copolymer comprises a first polymer block and a second polymer block.

5. The method of claim 4, wherein the first polymer block is polystyrene.

6. The method of claim 4, wherein the second polymer block is poly(4-vinylpyridine) or poly(2-vinylpyridine).

7. The method of claim 4, wherein the first polymer block is polystyrene and the second polymer block is poly(4-vinylpyridine).

8. The method of claim 1, wherein the applying is by solvent vapor annealing or thermal annealing.

9. The method of claim 1, wherein the substrate is selected from the group consisting of a metal, an alloy, a ceramic, a semiconductor, a plastic, a composite, a natural fiber, a synthetic fiber, glass, silicon, paper, wood, fabric, and quartz.

10. The method of claim 1, wherein the functionalizing agent is selected from the group consisting of benzyl bromide, benzyl chloride, 1,4-dibromobutane, 1,5-dibromopentane, 1,6-dibromohexane, 1,7-dibromoheptane, 1,8-dibromooctane, 1,9-dibromononane, 1,4-dichlorobutane, 1,5-dichloropentane, 1,6-dichlorohexane, 1,7-dichloroheptane, 1,8-dichlorooctane, 1,9-dichlorononane, and combinations thereof.

11. The method of claim 1, wherein the nanoparticle suspension comprises nanoparticles selected from the group consisting of Au, Ag, Pt, Cu, $Cu_2S$, CdS, CdSe, CdTe, ZnS, ZnSe, ZnTe, GaN, GaP, GaAs, GaSb, AlN, AlP, AlAs, AlSb, InP, InAs, InSb, $Fe_3O_4$, $Co_3O_4$, $NiFe_2O_4$, $CoFe_2O_4$, FePt, CoPt, FeNi, FeCo, Co, CoO, Ni, and NiO nanoparticles.

12. A method of producing a nanoparticle array comprising:
   (a) applying a block copolymer onto a substrate to give a thin film;
   (b) reacting the applied block copolymer of (a) with a functionalizing agent, wherein the functionalizing agent is an alkylating agent;
   (c) immersing the thin film of (b) in a nanoparticle suspension to give a nanoparticle array, wherein the nanoparticles are dispersed on the block copolymer; and
   (d) immersing the nanoparticle array of (c) in a growth solution, wherein the growth solution comprises a metal atom selected from the group consisting of Ag, Au, Cu, and Li or a non-metal selected from the group consisting of $SiO_2$, $TiO_2$, $Fe_2O_3$, $Al_2O_3$, Cds, CdSe, PbS, PbSe, and $Bi_2S_3$.

* * * * *